US008916586B2

(12) United States Patent
Kennedy et al.

(10) Patent No.: US 8,916,586 B2
(45) Date of Patent: Dec. 23, 2014

(54) ANTI-ANGIOGENIC COMPOUND

(75) Inventors: Breandan Kennedy, Dublin (IE);
Yolanda Alvarez, Valladolid (ES);
Jacintha O'Sullivan, Dublin (IE)

(73) Assignee: University College Dublin—National University of Ireland, Dublin, Dublin (IE)

( * ) Notice: Subject to any disclaimer, the term of this patent is extended or adjusted under 35 U.S.C. 154(b) by 0 days.

(21) Appl. No.: 13/979,447

(22) PCT Filed: Jan. 16, 2012

(86) PCT No.: PCT/IE2012/000002
§ 371 (c)(1),
(2), (4) Date: Jul. 12, 2013

(87) PCT Pub. No.: WO2012/095836
PCT Pub. Date: Jul. 19, 2012

(65) Prior Publication Data
US 2013/0289066 A1 Oct. 31, 2013

(30) Foreign Application Priority Data
Jan. 14, 2011 (IE) .................................. 2011/0017

(51) Int. Cl.
A61K 31/47 (2006.01)
A61K 31/4725 (2006.01)

(52) U.S. Cl.
CPC ............ *A61K 31/47* (2013.01); *A61K 31/4725* (2013.01)
USPC ........ 514/311; 514/186; 514/259.4; 514/314; 514/334; 546/152; 546/123; 544/282

(58) Field of Classification Search
USPC ...................... 514/311, 186, 259.4, 314, 334; 546/152, 123; 544/282
See application file for complete search history.

(56) References Cited

U.S. PATENT DOCUMENTS 6,413,998 B1 * 7/2002 Petrie et al. .................... 514/367

OTHER PUBLICATIONS

Kanczler et al. (European Cells and Materials, vol. 15, 2008, pp. 100-114.*
R. Zamboni et al., "Development of a Novel Series of Styrylquinoline Compounds as High-Affinity Leukotriene $D_4$ Receptor Antagonists: Synthetic and Structure-Activity Studies Leading to the Discovery of (±)            -3-[[[3-[2-(7-Chloro-2-quiriolinyl)-(E)-ethenyl]phenyl 1][[3-(dimethylamino)-3-oxopropyl]thio]methyl]thio]propionic Acid," 1992, J. Med. Chem., vol. 35, pp. 3832-3844.
T. Zsolnai, "Versuche zue entdeckung neuer fungistatika-vi," 1962, Biochemical Pharmacology, Pergamom Press Ltd., vol. 11, pp. 995-1016, abstract available.
K. Gagnidize et al., "Homology Modeling and Site-Directed Mutagenesis to Identify Selective Inhibitors of Endothelin-Converting Enzyme-2," 2008, J. Med. Chem., vol. 51, pp. 3378-3387.

(Continued)

*Primary Examiner* — Savitha Rao
(74) *Attorney, Agent, or Firm* — Jacobson Holman Hershkovitz, PLLC.

(57) ABSTRACT

A styrylquinoline derivative of structure I or IV or a benzodioxol isoquinoline of structure II or III for use in the treatment of an angiogenesis-related disease or disorder. The invention also provides a composition comprising a styrylquinoline derivative of structure I or IV or a benzodioxol isoquinoline of structure II or III for use as a medicament.

10 Claims, 21 Drawing Sheets

(56) References Cited

OTHER PUBLICATIONS

C. T. Bahner et al., "Hydroxy-,Nitro-,Amino-, and Methoxy-4-(4-dimethylaminostryl)quinolines[1],"Jul. 30, 1964, Carson-Newman College, pp. 267-271.
Y. Alvarez et al., "Selective Inhibition of Retinal Angiogenesis by Targeting P13 Kinase," 2009, PLoS One, vol. 4, No. 11, pp. 1-10.
Y. Alvarez et al., "Genetic determinants of hyaloids and retinal vasculature in zebrafish," 2007, BMC Developmental Biology, vol. 114, pp. 1-17.
G. Bergers et al., "Tumorigenesis and the Angiogenic Switch," 2003, Nature Reviews: Cancer, vol. 3, pp. 401-410.
G. Bergers et al., "Modes of resistance to anti-angiogenic therapy," Aug. 2008, Nature Review: Cancer, vol. 8, pp. 592-603.
Susan E. Brockerhoff, "Measuring the optokinetic response of zebrafish larvae," 2006, Nature Protocols, vol. 1, No. 5, pp. 2448-2451.
Peter Carmeliet, "VEGF as a Key Mediator of Angiogenesis in 10 Cancer," 2005, Oncology, vol. 69, pp. 4-10.
Christine Culy, "Bevacizumab: antiangiogenic cancer therapy", 2005, Drugs of Today, vol. 41, No. 1, pp. 23-36.
Jeroen den Hertog, "Chemical Genetics: Drug Screens in Zebrafish," Oct./Dec. 2005, Bioscience Reports, vol. 25, Nos. 5/6, pp. 289-297.
J. Doukas et al., "Topical Administration of a Multi-Targeted Kinase Inhibitor Suppresses Choroidal Neovascularization and Retinal Edema," Jul. 2008, J. Cell Physiol. vol. 216, No. 1, pp. 29-37.
Lee M. Ellis, "Antiangiogenic Therapy at a Crossroads: Clinical Trial Results and Future Directions,"Dec. 2003, Journal of Clinical Oncology, vol. 21, No. 23, pp. 281s-283s.
Napoleone Ferrara, "Vascular endothelial growth factor and age-related macular degeneration: from basic science to therapy,"Oct. 2010, Nature Medicine, vol. 16, No. 10, pp. 1107-1111.
N. Ferrera et al., "Angiogenesis as a therapeutic target," Dec. 2005, Nature, vol. 438, pp. 967-974.
Robert N. Frank, "Diabetic Retinopathy," Jan. 2004, The New England Journal of Medicine, vol. 350, No. 1, pp. 48-58.
Paul Goldsmith, "Zebrafish as a pharmacological tool: the how, why and when," 2004, Current Opinion in Pharmacology, vol. 4, pp. 504-512.
A. R. He et al., "Biologic Therapy for Colon Cancer," Jul. 2005, Clinical Advances in Hermatology and Oncology, vol. 3, No. 7, pp. 555-561.
R. D. Jager et al., "Age-Related Macular Degeneration," Jun. 2008, The New England Journal of Medicine, vol. 358, pp. 2606-2617.
M. E. Kleinman et al., "Sequence- and target-independent angiogenesis suppresion by siRNA via TLR3," Apr. 2008, Nature, vol. 452, pp. 591-597.
C. A. MacRae et al., "Zebrafish-Based Small Molecule Discovery," Oct. 2003, Chemistry & Biology, vol. 10, pp. 901-908.
M. Mandalá et al., "Oxaliplatin in Colon Cancer," Oct. 2004, The New England Journal of Medicine, vol. 351, pp. 1691-1692.
K. Nagarajan et al., "Some observations on the enantio- and diastereo-selective synthesis of 1-substituted-1, 2, 3, 4-tetrahydroisoquinolines," Mar.-Apr. 1994, Journal of the Indian Institute of Science, vol. 74, No. 2, pp. 247-256.
R. Narayanan et al., "Ranibizumab," Oct. 2006, Nature Reviews: Drug Discovery, vol. 5, pp. 815-816.
R. T. Peterson et al., "Chemical suppression of a genetic mutation in a zebrafish model of aortic coarctation," May 2004, Nature Biotechnology, vol. 22, No. 5, pp. 595-599.
F. B. Pichler et al., "Chemical discovery and global gene expression analysis in zebrafish," Aug. 2003, Nature Biotechnology, vol. 21, No. 8, pp. 879-883.
A. Rattner et al., "Macular degeneration: recent advances and therapeutic opportunities," Nov. 2006, Nature Reviews: Neuroscience, vol. 7, pp. 860-872.
K. Takahashi et al., "The Multi-targeted Kinase Inhibitor Pazopanib Causes Suppression and Regression of Choroidal Neovascularization," Apr. 2009, Arch. Ophthalmol., vol. 127, No. 4, pp. 494-499.
Siu-Fun Wong, "Cetuximab: an epidermal growth factor receptor monoclonal antibody for the treatment of colorectal cancer," 2005, Clinical Therapeutics, vol. 27, pp. 684-694.
L. I. Zon et al., "In vivo drug discovery in the zebrafish," Jan. 2005, Nature Reviews: Drug Discovery, vol. 4, pp. 35-44.

\* cited by examiner

3D 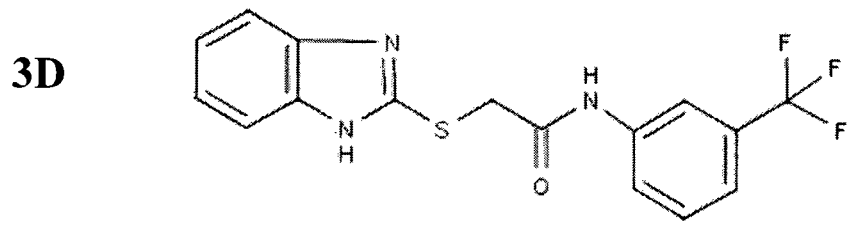
3F 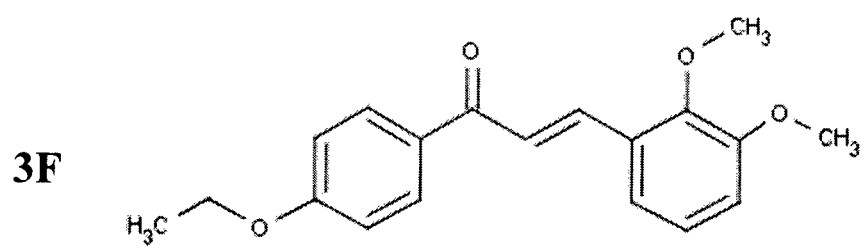
11F 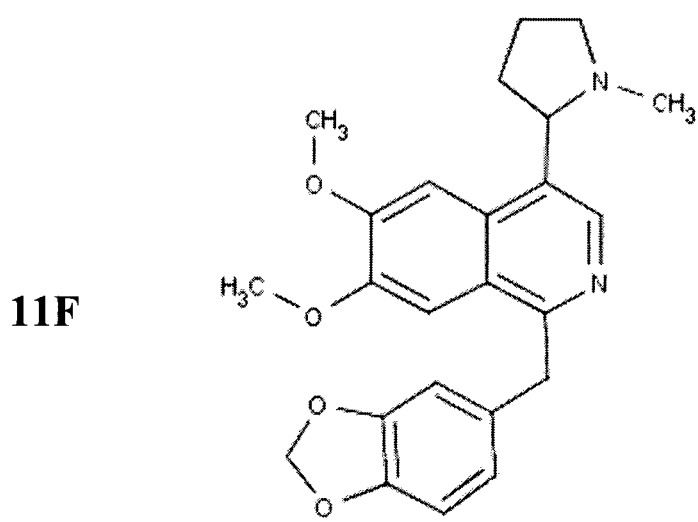
11B 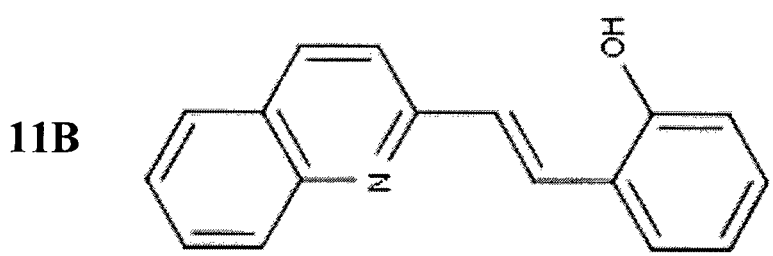
Fig. 2

A.
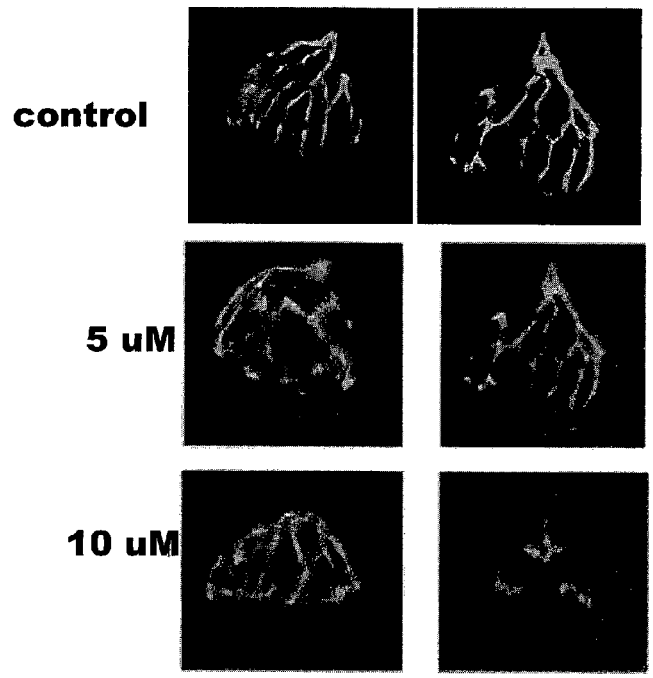
B.
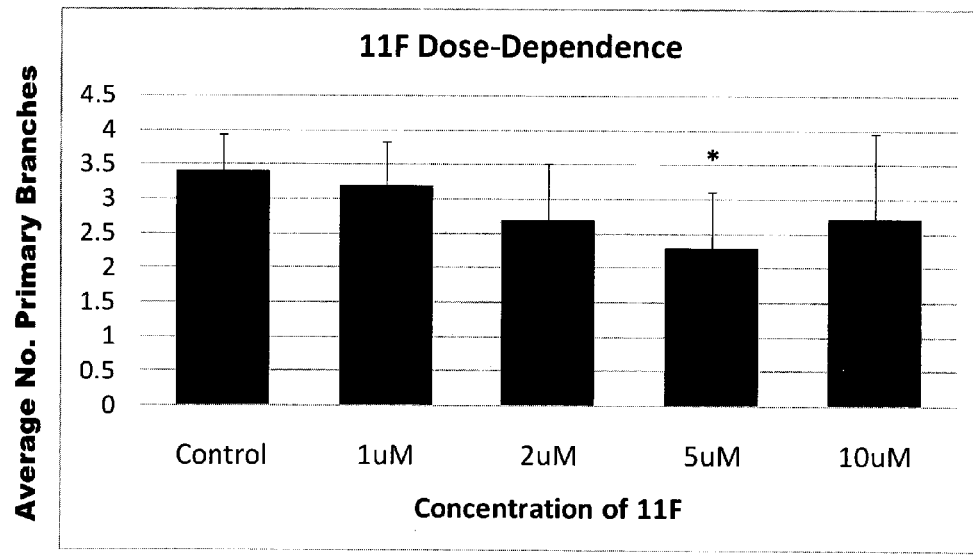
Fig. 3

11F & Intersegmental Vessel Angiogenesis

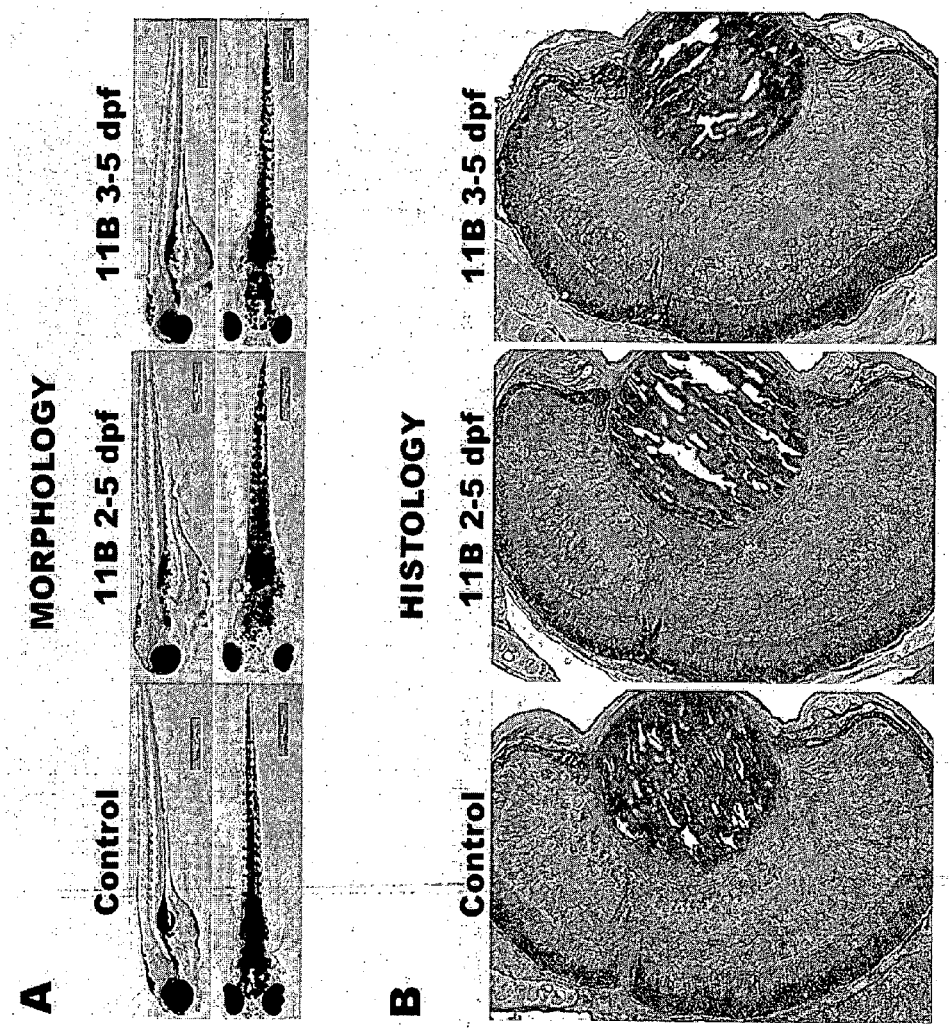
Fig. 9A-B

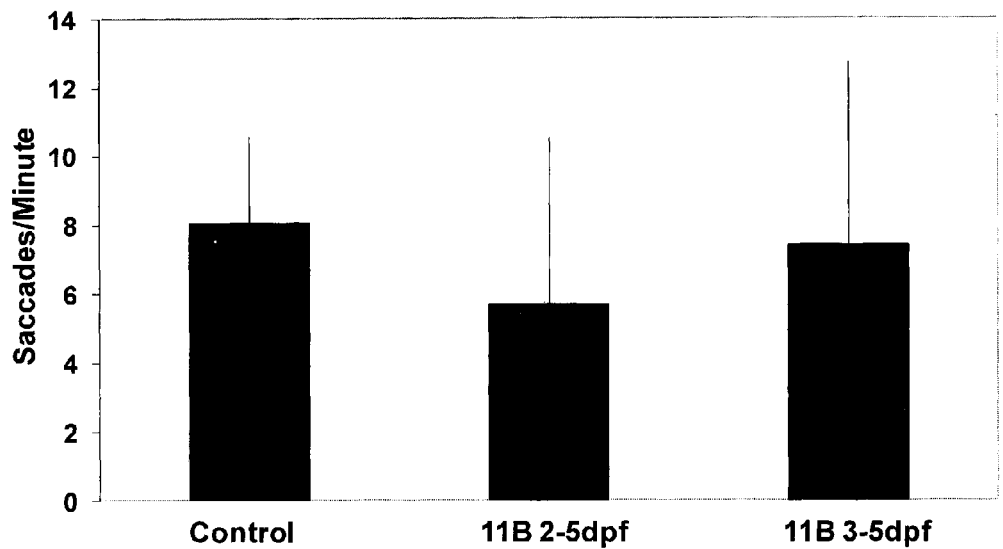
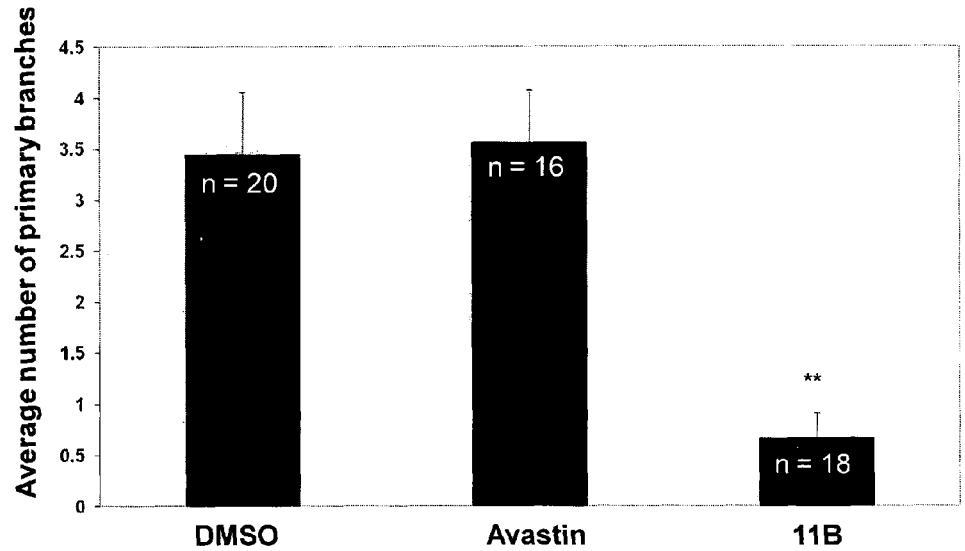
** P < 0.005
Fig. 9 C-D

11B & Intersegmental Vessel Angiogenesis

 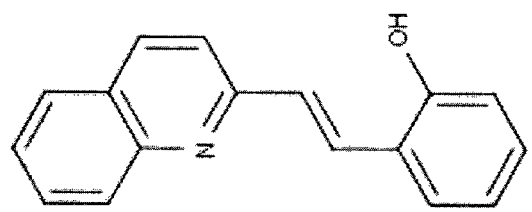
 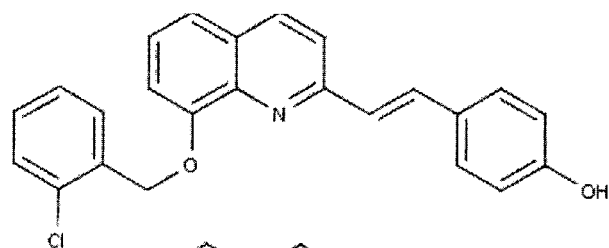
 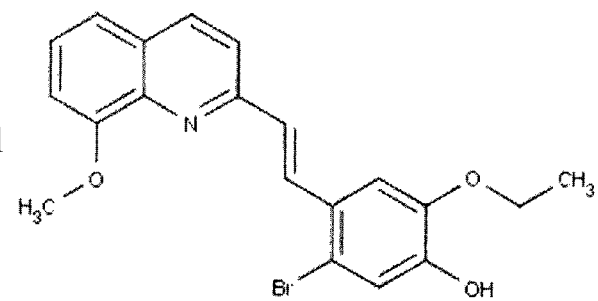
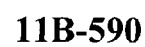 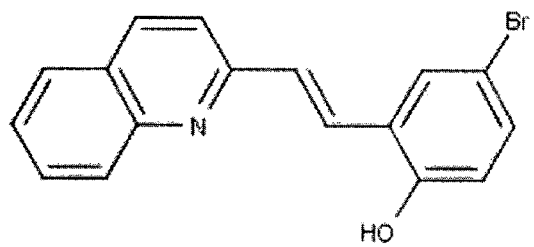
 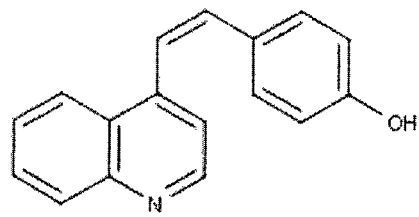
Fig. 11

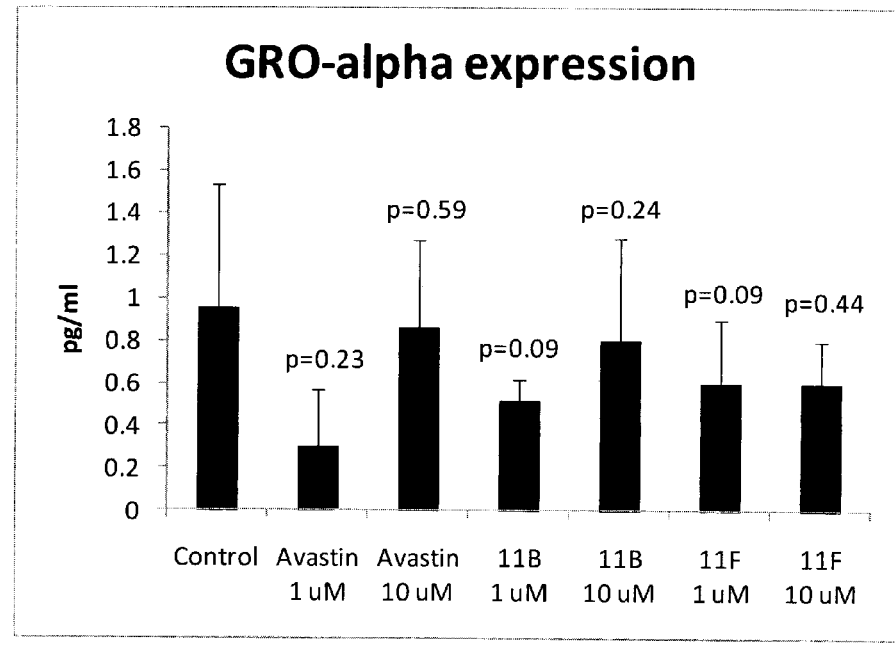
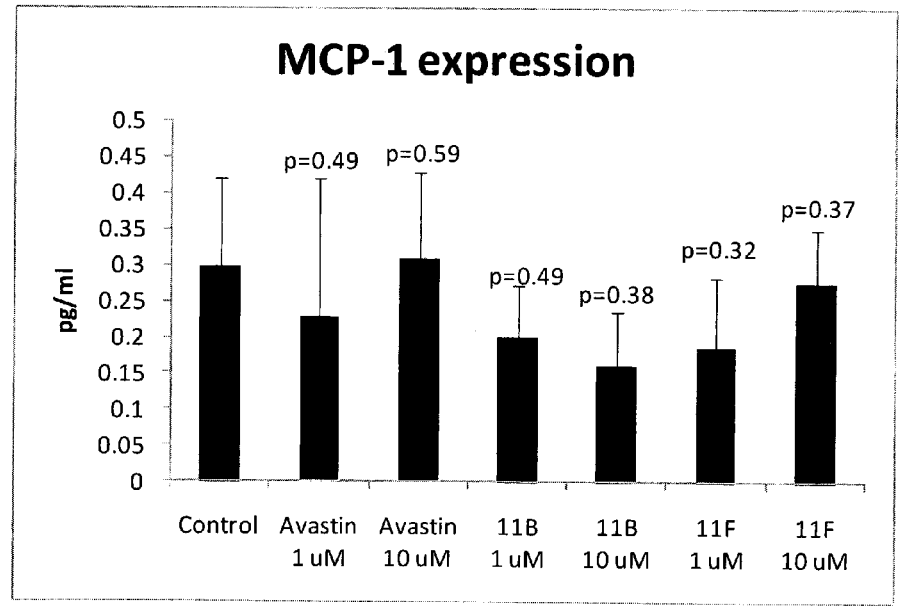
Fig. 16 A-B

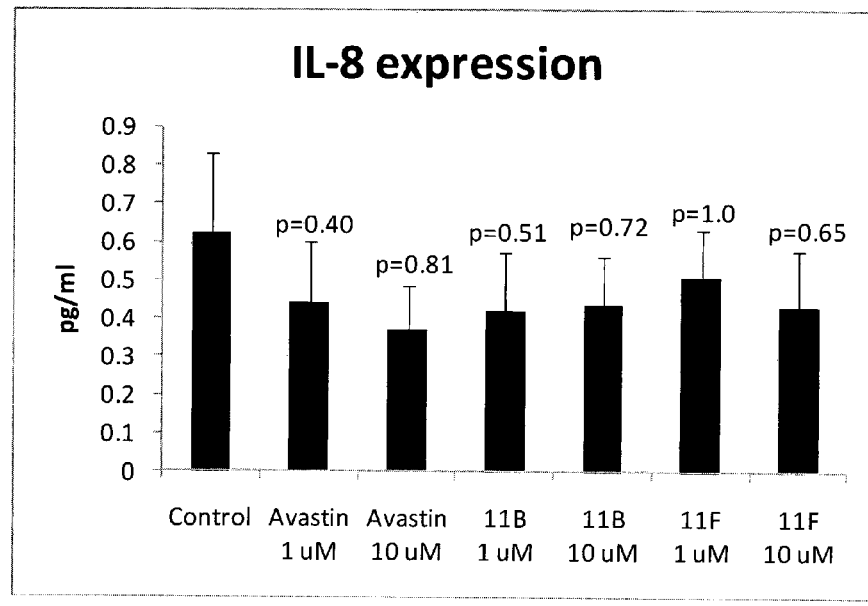
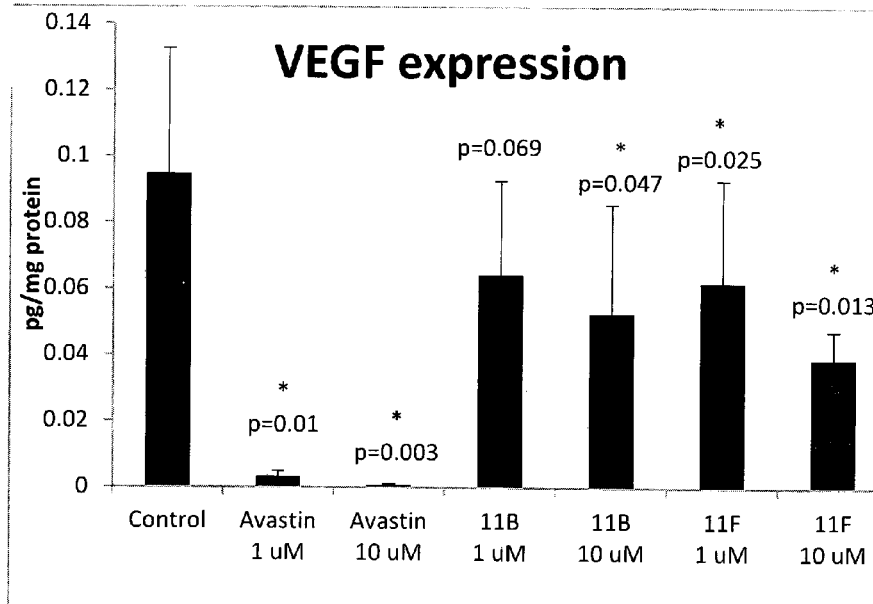
Fig. 16 C-D

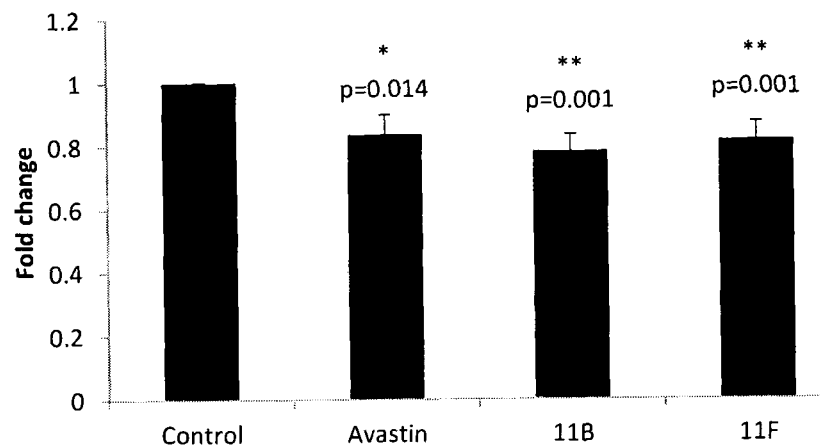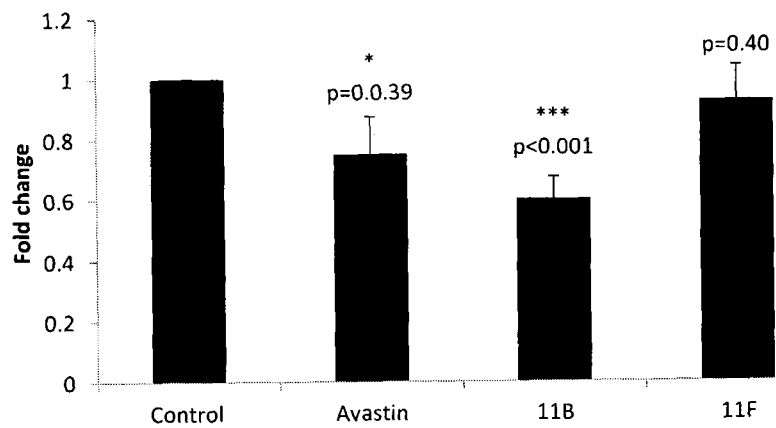
Fig. 16 E-F

ANTI-ANGIOGENIC COMPOUND

This is a national stage of PCT/IE12/000002 filed Jan. 16, 2012 and published in English, which has a priority of Irish no. 2011/0017 filed Jan. 14, 2011, hereby incorporated by reference.

INTRODUCTION

This invention relates to anti-angiogenic compounds.

In many human diseases there is an inappropriate growth of new blood vessels (angiogenesis). Angiogenesis is a physiological process involving the growth of new blood vessels from pre-existing vessels (Ferrara and Kerbel, 2005). Angiogenesis may be a therapeutic target for combating diseases characterised by poor vascularisation or abnormal vasculature (Ferrara and Kerbel, 2005). Targeted administration of specific compounds that may inhibit (anti-angiogenesis) or induce (pro-angiogenesis) the creation of new blood vessels in the body may help combat such diseases.

Diabetic retinopathy (DR) is the most feared complication of diabetes, compromising the quality of life in most sufferers (Frank, 2004). About 30% of type 1 diabetes patients advance to the blinding stage of the disease and about 60% of type 2 diabetes patients develop retinopathy. DR is the most common cause of vision impairment in people of working age in Western society and is likely to increase in prevalence as it has been projected that about 360 million people will suffer from diabetes by 2030. Diabetic macular oedema is the principal cause of vision loss in diabetes and involves leakage from a disrupted blood-retinal barrier.

Age-related macular degeneration (AMD) is a leading cause of vision loss in the western world among people aged 50 or older (Rattner and Nathans, 2006; Jager et al., 2008). Ninety percent of vision loss due to AMD results from the exudative form, which is characterized by newly formed blood vessels arising from capillaries in the choroid layer adjacent to the retina. Current approaches for resolving inappropriate growth of new vessels in the eye include laser treatment and molecular therapies targeted to vascular endothelial cell growth factor (VEGF) (Ferrara; Rattner and Nathans, 2006; Jager et al., 2008).

Photodynamic therapy (PDT) is a laser-based surgery for wet age-related macular degeneration. In PDT a light-sensitive dye is injected intravenously. A low energy laser beam is directed onto the target vessels. This makes the chemical react and destroy the leaking blood vessels without damaging adjacent healthy tissue however, multiple treatments are usually required and PDT is unsuitable for long-established wet age-related macular degeneration and cannot restore sight already lost to age-related macular degeneration.

There are a number of variations of VEGF molecular therapy but those in clinical use are antibodies targeted to VEGF which stop the development of new leaky blood vessels. Treatment requires intraocular injection by retinal specialists, needs to be repeated every six weeks and requires the patient to be sedated. In some cases, VEGF treatment has been shown to restore some visual acuity.

In diabetic retinopathy, laser ablation of the new vessels is routinely performed however laser ablation locally destroys the retina. In age-related macular degeneration monoclonal antibodies attenuating VEGF signalling are used clinically (Macugen, Lucentis), however the monoclonal antibodies are very expensive to manufacture/administer and patients require monthly intravitreal injections (Narayanan et al., 2006). Armala (pazopanib) is a multi-kinase (VEGF, PDGF, c-kit) angiogenesis inhibitor in clinical trials for AMD and cancer (Takahashi et al., 2009). siRNA targeting VEGF have also been used in clinical trials, however the siRNAs to VEGF have been found to act by a non-specific mechanism (Kleinman et al., 2008).

Cancer can originate in many tissues including the bowel, breast and skin. Obviously, with the prevalence and incurability of cancer types, there is a real need to develop new therapeutics. It is now widely accepted that the growth of solid tumours is dependent on their capacity to acquire a blood supply (Bergers and Benjamin, 2003). Indeed, much effort has been directed towards the development of anti-angiogenics that disrupt this process in tumours. In contrast to traditional anti-cancer agents that directly destroy tumour cells, mediating a cytocidal effect, anti-angiogenics are generally regarded as cytostatic agents. Another emerging feature of the use of anti-angiogenics in cancer treatment is the phenomenon of resistance (Bergers and Hanahan, 2008). In both animal models and humans, the benefits of anti-angiogenic therapy are at best transitory and commonly followed by a restoration of tumour growth and progression. As such, there is a pressing need to find multiple target points for anti-angiogenic therapy, so as to provide additional opportunities to pre-empt such resistance phenomena emerging.

Of particular relevance is Colorectal Cancer (CRC) which accounts for 10-15% of all cancers and is the leading cause of cancer deaths in the Western world (Mandala et al., 2004). Colorectal cancer is the commonest internal cancer in the Western World. It is a major cause of morbidity and mortality, with approximately 50 percent dying from their disease within 5 years of diagnosis. Contemporary chemotherapy treatments are effective in many cases but extremely expensive and potentially dangerous.

Current treatments for colorectal cancer patients are complex. Multidisciplinary teams must decide who will benefit from expensive new treatments. Currently, treatment decisions for patients depend solely on pathological staging. The chemotherapeutic agents Fluorouracil (5-FU) plus leucovorin (LV) have been the mainstay treatment for CRC. Newer drugs such as oxaliplatin, capecitabine and irinotecan have significantly improved response rates, time to progression and increase survival rates in patients with advanced CRC (Mandala et al., 2004). However, even with these new drug combinations, the long term prognosis remains poor for late-stage CRC patients with metastatic lesions.

Over the last few years, new monoclonal antibody therapies targeting key angiogenic molecules including: bevacizumab (Avastin, anti-VEGF) and cetuximab (Erbitux, anti-EGFR) (Culy, 2005; He and Marshall, 2005) have been introduced to fight late-stage CRC and improve outcome (Ellis, 2003). Bevacizumab (Avastin) blocks vascular endothelial growth factor (VEGF) by preventing the interaction of VEGF with its' receptors [VEGFR-1 (Flt-1) and VEGFR-2 (KDR)]. Pre-clinical studies suggest that bevacizumab acts by inhibiting tumour neo-vascularisation and when used in combination with chemotherapeutic drugs, it increases the permeability of tumours to chemotherapy (Ellis, 2003). Cetuximab (Erbitux) inhibits the epidermal growth factor receptor (EGFR) signalling cascade (Wong, 2005) and tumours that over-express EGFR have a poor prognosis. Erbitux also inhibits angiogenesis inside tumours, leading to an overall suppression of tumour growth (Carmeliet, 2005). Pre-clinical data indicate that Erbitux has anti-tumour activity in colon cancer xenografts and can reduce the production of VEGF, interleukin-8 (IL-8), and basic fibroblast growth factor (bFGF). Currently, these molecular therapies are solely given to late-stage metastatic CRC patients

STATEMENTS OF INVENTION

According to the invention there is provided a compound of structure I or IV

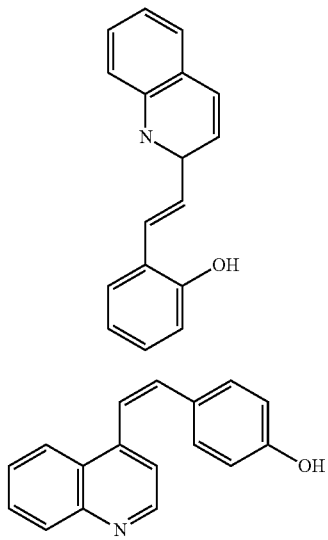

(I)

(IV)

for use in the treatment of an angiogenesis-related disease or disorder.

The invention also provides a compound of structure II or III

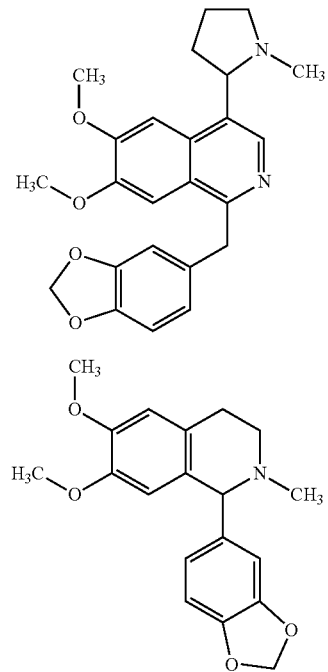

(II)

(III)

for use in the treatment of an angiogenesis-related disease or disorder.

Structure II which is also referred to in the examples as 11F and structure III which is referred to as 11F-522 in the examples share some common features.

Both compounds contain; a) a basic nitrogen group; b) a fused electron-rich aromatic ring; and c) a second pendant electron-rich aromatic ring.

Both molecules contain a chiral centre. As a result the compounds were originally tested as a 50:50 (racemic) mixture of the following two individual enantiomers.

The chemical name of 11F-522 is 1-(1,3-benzodioxol-5-yl)-6,7-dimethoxy-2-methyl-1,2,3,4-tetrahydroisoquinoline.

The structure of 11F-522 enantiomer (S)-(+)-1-(1,3-benzodioxol-5-yl)-6,7-dimethoxy-2-methyl-1,2,3,4-tetrahydroisoquinoline (Enantiomer 1) and the structure of 11F-522 enantiomer (R)-(−)-1-(1,3-benzodioxol-5-yl)-6,7-dimethoxy-2-methyl-1,2,3,4-tetrahydroisoquinoline (Enantiomer 2) is as follows.

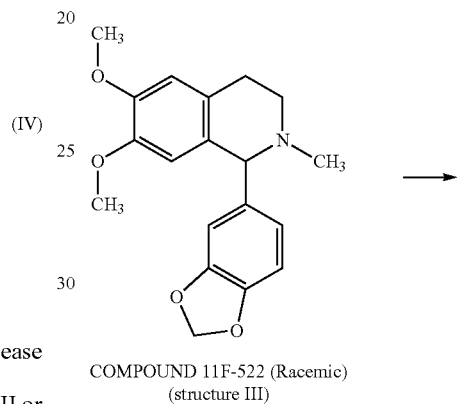

COMPOUND 11F-522 (Racemic)
(structure III)

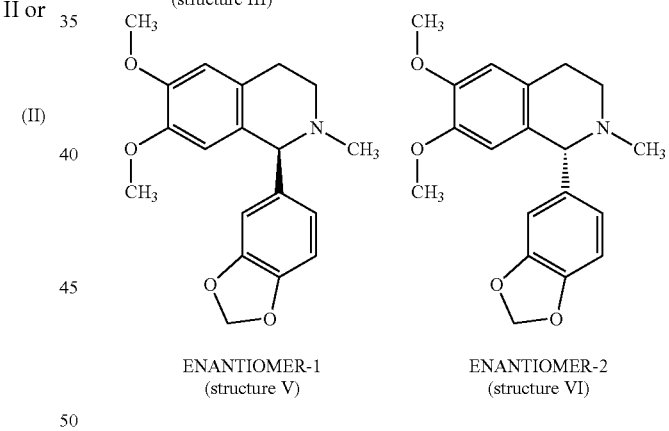

ENANTIOMER-1
(structure V)

ENANTIOMER-2
(structure VI)

The individual enantiomers of 11F-522 can be separated from a racemic mixture of 11F-522 in accordance with the methodology described in Nagarajan et al, 1994.

The compounds may be used in a method of reducing or inhibiting angiogenesis in a subject having a pathological condition associated with angiogenesis.

Structure (II) may be in the form of a single enantiomer or a mixture of the two individual enantiomers thereof.

Structure (IV) may be in the form of a single enantiomer or a mixture of the two individual enantiomers thereof.

The angiogenesis-related disease or disorder may be associated with neovascularisation of the eye. The angiogenesis-related disease or disorder may be associated with blindness. The angiogenesis-related disease or disorder may be age-related macular degeneration such as wet age-related macular degeneration or diabetic retinopathy.

The angiogenesis-related disease or disorder may be cancer. The cancer may be a solid tumour forming cancer. The cancer may be colorectal cancer.

The invention also provides a composition comprising a compound of structure I or IV

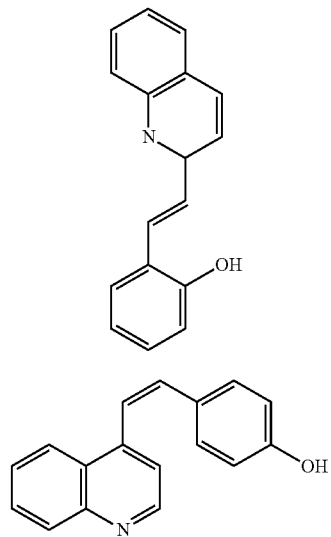

for use as a medicament.

The invention further provides a composition comprising a compound of structure II or III

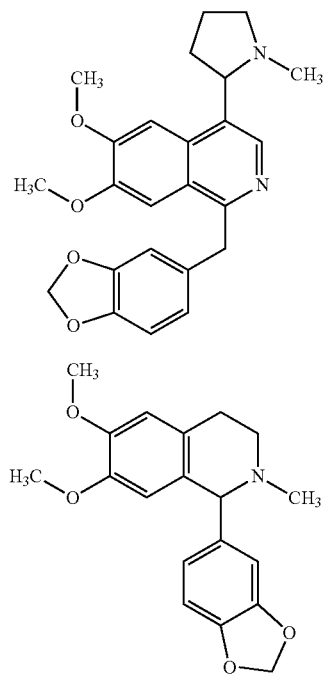

for use as a medicament.

The compound of structure (II) in the composition may be in the form of a single enantiomer or a mixture of the two individual enantiomers thereof.

The compound of structure (IV) in the composition may be in the form of a single enantiomer or a mixture of the two individual enantiomers thereof.

The composition may further comprise a pharmaceutically acceptable excipient.

The composition may be in a form for topical administration. The composition may be in the form of eye drops.

The composition may be in a form for systemic administration. The composition may be in the form of an injectable solution or suspension.

The invention also provides for the use of a composition described herein in the treatment of an angiogenesis-related disease or disorder. The angiogenesis-related disease or disorder may be associated with neovascularisation of the eye. The angiogenesis-related disease or disorder may be associated with blindness. The angiogenesis-related disease or disorder may be age-related macular degeneration such as wet age-related macular degeneration or diabetic retinopathy. The angiogenesis-related disease or disorder may be cancer. The cancer may be a solid tumour forming cancer. The cancer may be colorectal cancer.

In accordance with the invention, the angiogenesis-related disease or disorder may be diseases or disorders associated with pathological angiogenesis for example, opthalmic diseases or angiogenesis-dependent cancers. Opthalmic diseases include eye disease associated with ocular neovascularisation such as angiogenic ophthalmic diseases associated with blindness for example age-related macular degeneration and diabetic retinopathy. The age-related macular degeneration may be wet age-related macular degeneration. Angiogenesis-dependent cancers include solid tumour forming cancers in which growth of the solid tumour is dependent on their capacity to acquire a blood supply, for example colorectal cancer.

The compounds and compositions described herein may be used in the treatment of diseases or disorders associated with undesirable inflammation, for example arthritis or rheumatoid arthritis.

The compounds and compositions described herein can be considered to be anti-angiogenic compounds and compositions.

Also described is the use of a compound of structure I or IV

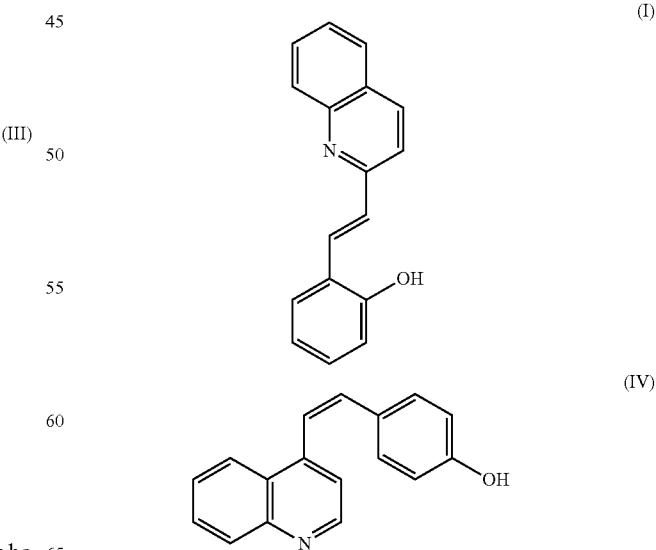

in the treatment of angiogenesis.

The use of a compound of structure II or III

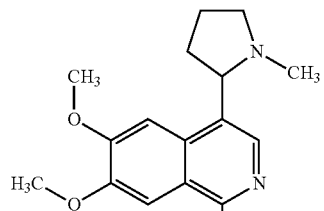
(II)

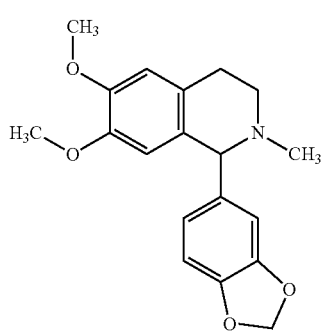
(III)

in the treatment of angiogenesis is also described.

The angiogenic driven condition or disease may be associated with neovascularisation of the eye, for example the angiogenic driven disease may be associated with blindness such as age-related macular degeneration or diabetic retinopathy.

The angiogenic driven disease may be associated with cancer, for example the angiogenic driven disease may be associated with a solid tumour. The angiogenic driven disease may be colorectal cancer.

The compound described herein may be used in the treatment of undesirable inflammation.

Also described is a pharmaceutical composition comprising a compound of structure I or IV

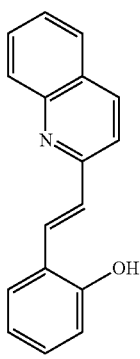
(I)

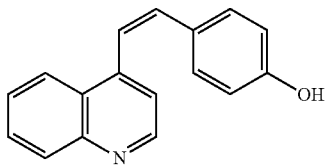
(IV)

and a pharmaceutically acceptable excipient.

A pharmaceutical composition comprising a compound of structure II or III

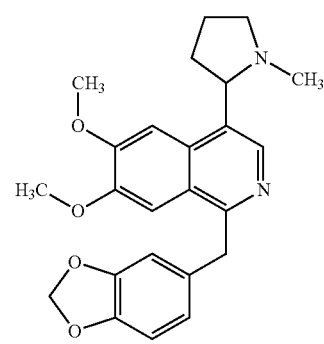
(II)

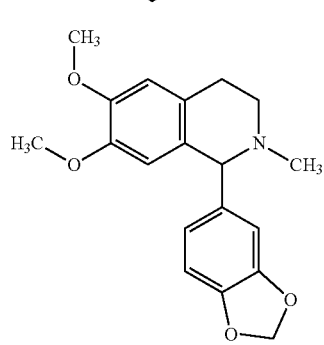
(III)

and a pharmaceutically acceptable excipient is also described.

The pharmaceutical composition may be in a form for topical administration such as in the form of eye drops.

The pharmaceutical composition may be in a form for systemic administration such as in the form of an injectable solution or suspension.

A pharmaceutical composition as described herein may be used in the treatment of angiogeneis.

The angiogenic driven disease may be associated with neovascularisation of the eye. The angiogenic driven disease may be associated with blindness. The angiogenic driven disease may be age-related macular degeneration or diabetic retinopathy.

The angiogenic driven disease may be associated with cancer. The angiogenic driven disease may be associated with a solid tumour. The angiogenic driven disease may be colorectal cancer.

A pharmaceutical composition as described herein may be used in the treatment of undesirable inflammation.

A compound or pharmaceutical composition as described herein may be used in the treatment of an angiogenic driven disease (angiogenic-related disease or disorder) and/or undesirable inflammation.

Also described is a method of treating an angiogenic driven disease (angiogenic-related disease or disorder) and/or undesirable inflammation comprising the step of administering a therapeutically effective amount of a compound or composition described herein to a mammal in need thereof. The mammal may be a human.

The invention further provides for biologically active salts of compounds I, II, III, IV, V and VI.

The compounds and compositions of the invention may be administered by any conventional route for example parenterally such as in the form of an injectable solution or suspension, enterally for example orally such as in the form of an oral dosage form for example a tablet or a capsule, or topically for example in the form of lotions, gels, ointments, creams or eyedrops. The compounds or compositions of the invention may also be administered in a nasal or suppository form. The route of administration of the compounds and compositions of the invention will depend on the angiogenic driven disease (angiogenic-related disease or disorder) and/or the undesirable inflammation to be treated.

It will be appreciated by a person skilled in the art that the compounds and compositions of the invention should be administered in a therapeutically effective amount. The dosage of the active ingredient will depend on a variety of factors including type, species, age, weight, sex, medical condition of the patient, the severity of the condition to be treated and the route of administration.

BRIEF DESCRIPTION OF THE DRAWINGS

The invention will be more clearly understood from the following description of an embodiment thereof, given by way of example only, with reference to the accompanying drawings, in which:

FIG. 2 shows the chemical structures of compounds 3D, 11F, 3F and 11B identified as lead anti-angiogenic compounds in screens for inhibitors of developmental angiogenesis in zebrafish;

FIG. 3 shows the dose-response effect of lead 11F in relation to developmental angiogenesis of the hyaloid vasculature in zebrafish. (A) Representative epi-fluorescent images of dissected zebrafish lenses, depicting the patterns of hyaloid vasculature observed in zebrafish larvae treated with 5 or 10 µM 11F. (B) Graph of the average number of primary branches of hyaloid vasculature following treatment of larvae with increasing concentrations of 11F. 5 µM 11F results in a significant inhibition of hyaloid vasculature development (p<0.005). n=10 (1, 2, 5 uM), n=7 (10 uM) and n=5 (control;

FIG. 9(A) are bright field microscopy images showing normal wholemount morphology in the presence and absence of 10 µM compound 11B (larvae treated from day 2-5 or day 3-5); (B) are bright field microscope images of retinal sections in the presence and absence of 10 µM compound 11B; (larvae treated from day 2-5 or day 3-5). (C) is a graph showing visual function as measured by the optokinetic response (OKR) is not statistically different from controls when treated with compound 11B from day 2-5 or day 3-5 and (D) is a graph showing that in zebrafish, 10 µM compound 11B induces a more effective anti-angiogenic effect than Avastin as measured by the number of primary hyaloid branches;

FIG. 11 shows the chemical structures of 4 compounds related to 11B that were used for a structure-activity relationship study;

FIGS. 16A to F are bar charts demonstrating that 11B and 11F have significant effects on the levels of specific angiogenic/inflammatory factors secreted from explants cultures of human colorectal cancers. 1 and 10 µM Avastin, a clinically used anti-angiogenic, has significant effects on the levels of vascular endothelial growth factor (VEGF) and interleukin 6 (IL-6) secreted by the human tumour explants. 1 µM 11B significantly reduces the levels of IL-6, whilst 10 µM 11B significantly reduces the levels of VEGF, IL-6 and interleukin 1 beta (IL-1b) secreted by the human tumour explants. 1 µM 11F significantly reduced the levels of VEGF, whilst 10 µM 11F significantly reduced the levels of VEGF and IL-1b, secreted by the human tumour explants. n≥4 patients for VEGF, IL-8, MCP-1 & GRO-alpha, n=20 patients for IL-1b & IL-6.

DETAILED DESCRIPTION

Figure 1A:
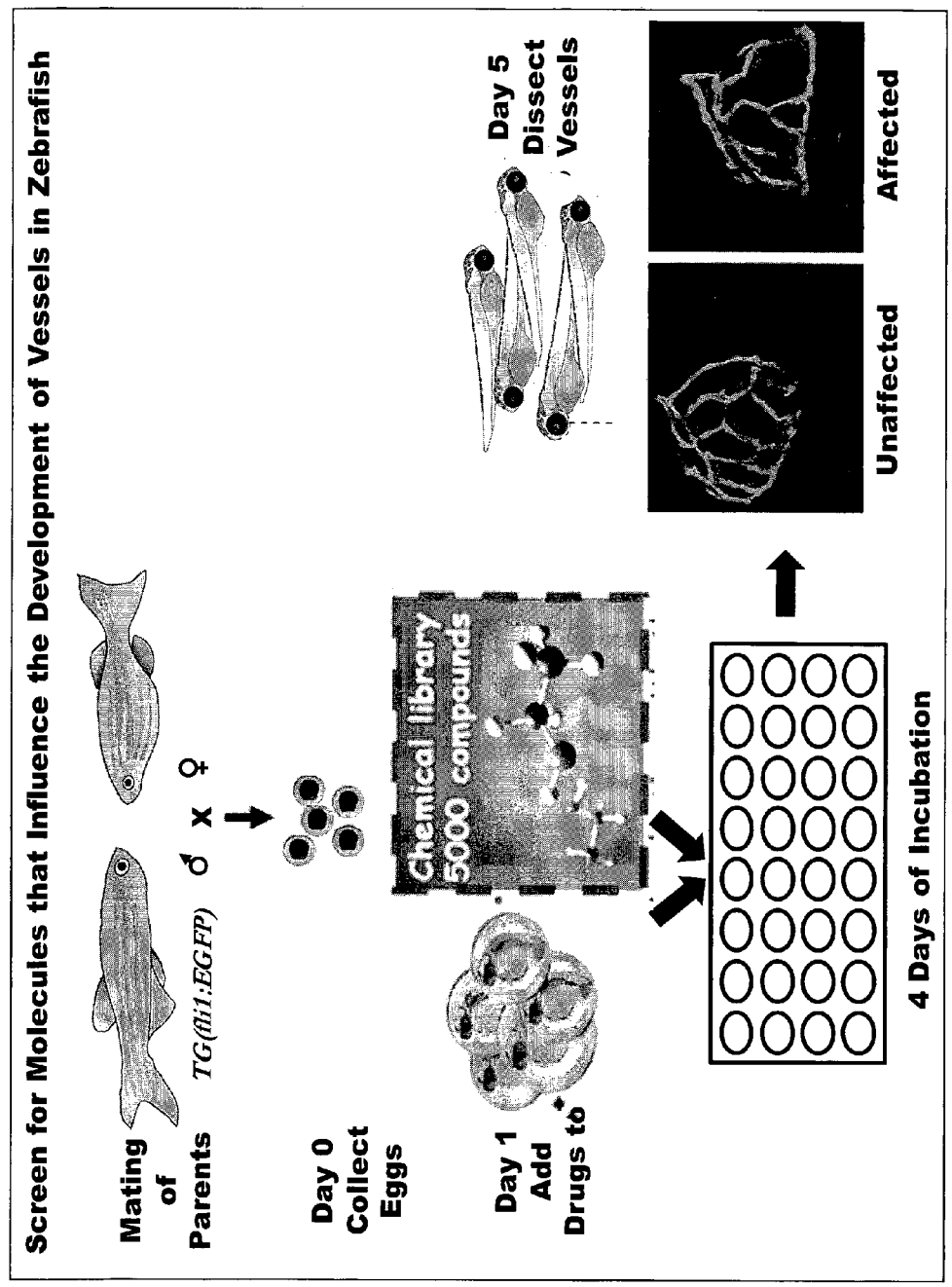
FIG. 1A is a schematic showing a screen for small molecules inhibiting developmental angiogenesis in the zebrafish eye, 1 day old eggs are incubated in multi-well plates with the chemicals from a library of small molecules. At day 5, larvae are euthanized, the eyes dissected and the developing hyaloid vessels which are attached to the lens analysed; (B) epi-fluorescent microscope images of selected lead compounds from the screen. Archetypal structure of the hyaloid vessels attached to the dissected lens in a 5 day old larvae is shown in the top-left panel (control) followed by 4 selected leads that inhibit intraocular angiogenesis (in order of increasing anti-angiogenic effect: 3D, 11F, 3F and 11B)

We have identified small molecule compounds that exhibit an anti-angiogenic effect, in vivo. The anti-angiogenic compounds may be used to treat inappropriate blood vessel formation (neovascularisation) such as the neovascularisation associated with debilitating forms of human blindness, including age-related macular degeneration (AMD) and diabetic retinopathy (DR). Additionally, this compound may have therapeutic benefits in cancer, by cutting off the blood supply to tumours or by inhibiting the secretion of angiogenic and/or inflammatory factors from a tumour.

The compound may be administered to patients with diseases characterised by neovascularisation such as forms of progressive blindness that would benefit from stunting the growth of inappropriate new blood vessels, or cancer patients in which tumour growth can be halted by cutting off blood supply or by inhibiting the secretion of angiogenic and/or inflammatory factors from the tumour.

The anti-angiogenic compounds described herein have the potential to offer patients effective, easily administered, safe and cost-effective treatments to prevent vision loss and tumour growth The compounds described herein effectively inhibit new vessel growth. In the case of anti-angiogenic treatments for the eye, the compounds have the potential to be administered in the conventional manner as an injection or as eye drops as their small chemical size facilitates absorption from the cornea unlike antibodies which require intravitreal injection. Similar-sized small molecules have been shown to exhibit anti-angiogenic efficacy in the eye upon topical administration (Doukas et al., 2008).

Topical administration of the compound, such as through eye drops, will eliminate the repeated injections that are required for the administration VEGF antibodies will reduce the safety risks associated with repeated intra vitreal injections. Furthermore, small molecule compounds will be cheaper to manufacture than antibodies and unlike antibodies, no potentially hazardous biological components are required to synthesise the compounds which will reduce the manufacturing costs and regulatory safety requirements.

We have used the zebrafish model as an in vivo screen for chemical libraries as the small size and transparency of the zebra fish enables high-content screens in multi-well plate formats (MacRae and Peterson, 2003; Pichler et al., 2003; Peterson et al., 2004; den Hertog, 2005; Zon and Peterson, 2005). Furthermore, many drugs have been shown to have comparable actions in humans and zebrafish including aspirin, warfarin, L-NAME, carbachol and diazepam (Goldsmith, 2004). To identify anti-angiogenic drugs we used a transgenic line of zebrafish that expresses a fluorescent reporter (EGFP) specifically in vasculature (Tg(fli1:efgp)). This line was obtained from the Zebrafish International Resource Center. Our assay involved screening the effect of drugs in the library on the development of blood vessels in zebrafish. Specifically, we looked at the integrity of vessels developing in the eye (hyaloid vessels attached to the lens) and in the trunk. From these screens we have identified lead compounds from a library of about 1600 compounds that exhibited reproducible anti-angiogenic activity in vivo. Our characterisation of lead compounds was based on significant inhibition of hyaloid vessel formation in terms of pattern or primary branch number.

The invention will be more clearly understood from the following examples thereof.

EXAMPLES

Example 1

Screening Chemical Libraries

All experiments were carried out under ethical approval granted by the UCD animal research ethics committee.

Tg(fli1:EGFP) zebrafish were maintained according to standard procedures on a 14 hr light/10 hr dark cycle at 28° C. Referring to the schematic of FIG. 1A, embryos were obtained by natural spawning and developmental stages established by time and morphological criteria. A chemical library containing numerous compounds was screened (FIG. 1A). In this specific example, the chemical library contained 5000 compounds of the DIVERSet™ collection from ChemBridge Corp., USA. At 24 hours post fertilisation (hpf), 5 embryos per well were placed in 400 ml of Embryo Medium/1% DMSO and incubated with drug at 28° C. on a 14 h light/10 h dark cycle. Larvae were euthanised, and fixed in 4% PFA at 4° C. overnight before analysis. (FIG. 1A).

Example 2

Quantification of Primary Branch Number

Prior to analysis of the intraocular vasculature, the control and treated larvae were observed under an Olympus SZX16 stereo zoom microscope and screened for general malformations. Overall patterning of the vasculature (fin, gut and intersegmental vessels) was examined for abnormalities (FIGS. 7B and 9A).

Figure 1B:
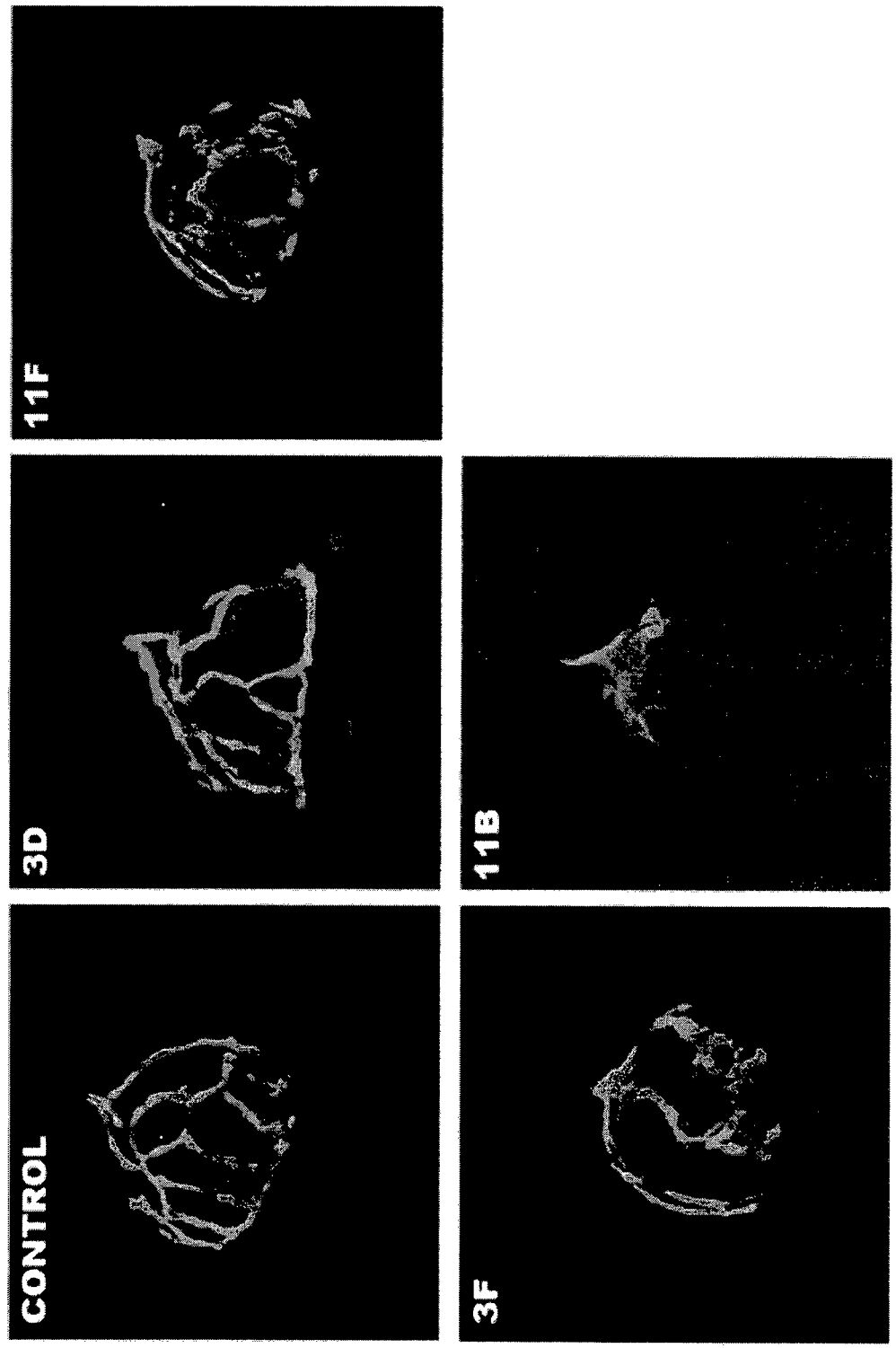

Right lenses were dissected from the larvae and transferred to depression slides for observation under epi-fluorescence in the Olympus SZX16 and to cover-slip bottom Petri-dishes for confocal microscopy in a Zeiss UV510 META LSM system (20× and 40× inverted objectives). To achieve appropriate orientation, lenses were embedded in 10% methyl-cellulose and manipulated with a tungsten needle (0.5 mm diameter). Patterning of the hyaloid vessels on the treated larval lenses was compared to DMSO controls and the archetypal pattern previously described (Alvarez et al., 2007; Alvarez et al., 2009). The number of primary vessels radiating from the back of the lens (3-4 main branches at 5 dpf in controls and previously described), was counted and the average number was graphed for each drug. From screens of ~1600 small molecules, four "hits" that inhibited the number of primary hyaloids vessels were identified (FIG. 1B). The chemical structures of these compounds are shown in FIG. 2.

Example 3

Quantification of Intersegmental Vessel Number & Larval length

Figure 4:
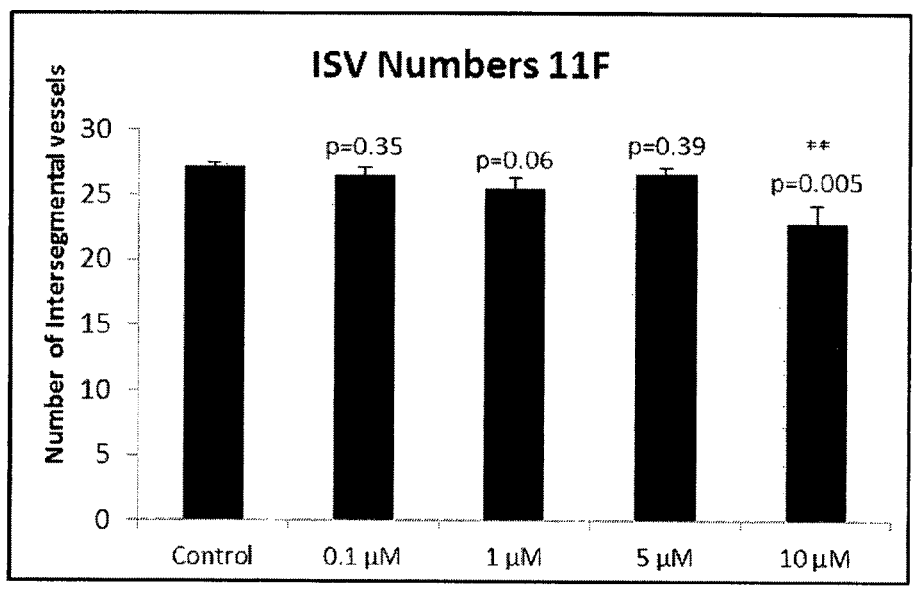
FIG. 4 shows that 10 µM 11F added at 6 hours post-fertilisation causes a modest but significant inhibition of developmental angiogenesis of the trunk intersegmental vessels. n≥5 for all samples.
Figure 10:
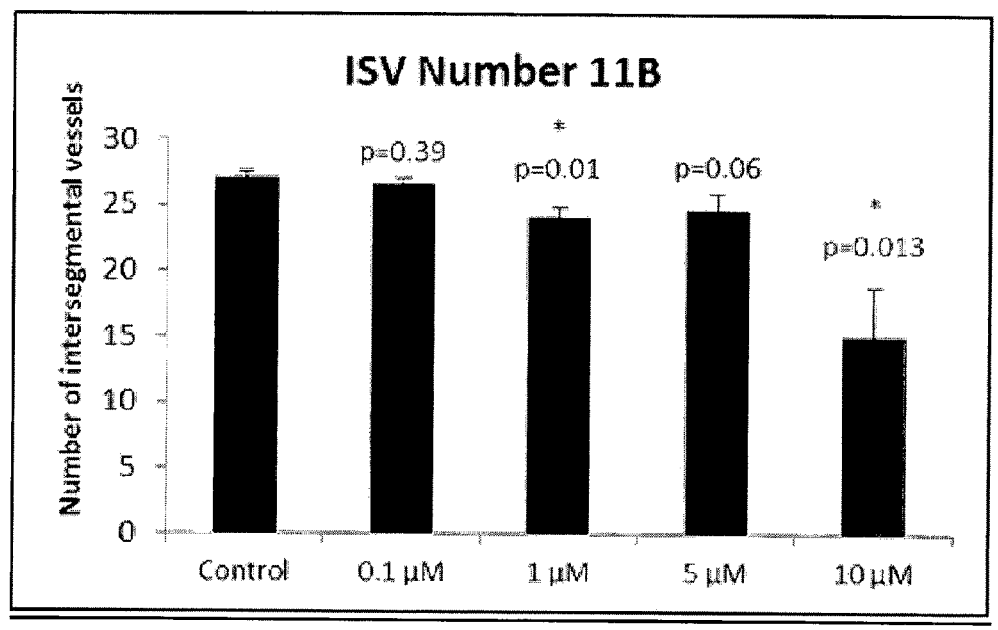
FIG. 10 shows that 10 µM 11B added at 6 hours post-fertilisation causes significant inhibition of developmental angiogenesis of the trunk intersegmental vessels. n≥5 for all samples.

At 6 hours post fertilisation, 5 embryos per well were placed in 400 µL of Embryo Medium/1% DMSO and incubated with a range of drug concentrations (0.1-10 µM) at 28° C. on a 14 h light/10 h dark cycle. Larvae were manually dechorionated, euthanised, and fixed in 4% PFA at 4° C. overnight before analysis. The larvae were then washed with PBS and transferred to depression slides for observation under epi-fluorescence in an Olympus SZX16 fluorescent microscope. The number of intersegmental vessels was counted and the average number was graphed for each drug. 11B and 11F inhibit developmental angiogenesis of zebrafish intersegmental vessels in a dose-dependent and statistically significant manner (FIGS. 4 and 10). At the highest concentration (10 µM), 11B was seen to inhibit intersegmental vessel formation by 44%. 11F inhibited intersegmental vessel formation by 16% at the highest concentration (10 µM).

Example 4

Validation of Anti-Angiogenic Leads

Figure 7:
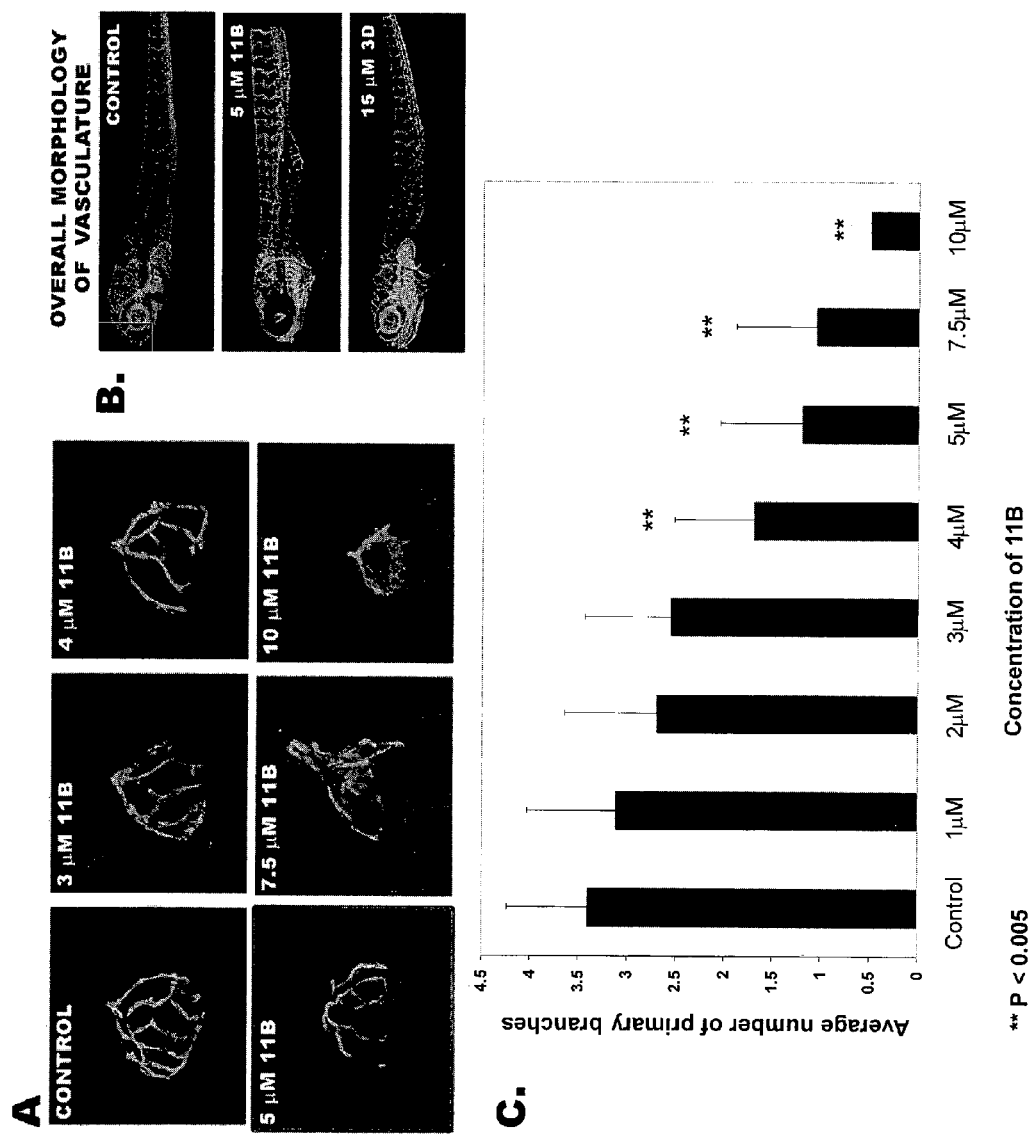
FIG. 7 shows the dose-response inhibition of lead 11B in relation to developmental angiogenesis of the hyaloid vasculature in zebrafish. (A) Representative epi-fluorescent images of dissected zebrafish lenses, demonstrating a dose-dependent inhibition of the patterning of the hyaloid vasculature in zebrafish larvae treated with 3-10 µM 11B. (B) Representative epi-fluorescent images of whole larvae following treatment with 11B demonstrates that the drug is not toxic as the gross morphology is normal and indicates that 11B effects newly forming vessels but not existing vessels as the intersegmental vessels along the trunk of the treated fish are intact. (C) Graph of the average number of primary branches of hyaloid vasculature following treatment of larvae with increasing concentrations of 11B. 4, 5, 7.5 or 10 µM 11B results in a significant inhibition of hyaloid vasculature development (p<0.005). n≥8 for all treatment groups.

To validate the "hits" from the library screen, dose-dependence experiments were conducted by screening the drugs in the assay described in Example 2 above but at a range of increasing concentrations between 1-10 µM. Larvae were maintained under the drug treatments at 28° C. on 14 hr light/10 hr dark cycle until 5 days post fertilisation (dpf), when they were euthanised and fixed in 4% PFA at 4° C. overnight before analysis. The average number of primary hyaloids branches was graphed for each concentration of drug. Compounds 3D and 3F, two of the "hits" from the primary library screen, did not exhibit a dose-dependent response and were discarded. However, compounds 11B and 11F did inhibit developmental angiogenesis of the zebrafish hyaloid vasculature in a dose-dependent and statistically significant manner and were therefore chosen as lead drugs for further characterisation (FIGS. 3 and 7). One of the lead compounds identified by the screen of chemical library was 11B which has the chemical name 2-[2-2-quinolinyl)vinyl]phenol and its structure shown below:

Structure I (compound 11B)

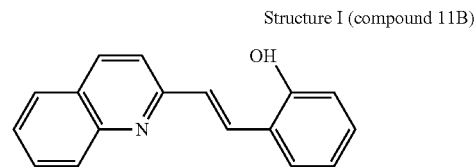 [SMILES: Oc1ccccc1/C=C/c1ccc2ccccc2n1]

The other lead compound identified was 11F which has the chemical name 1-(1,3-benzodioxol-5-yl methyl)-6,7-dimethoxy-4-(1-methyl-2-pyrrolidinyl)isoquinoline and its chemical structure is shown below.

Structure II (compound 11F)

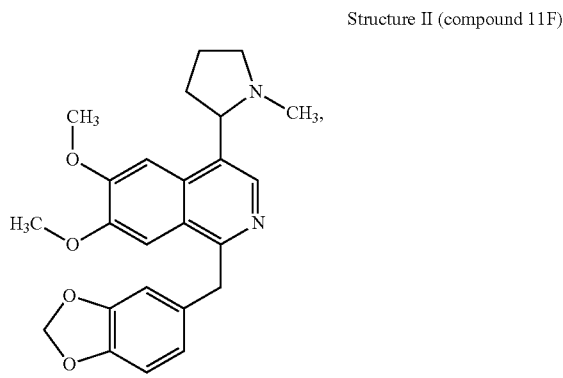 [SMILES: COc1cc2c(C3CCCN3C)cnc(Cc3ccc4c(c3)OCO4)c2cc1OC]

Figure 8:
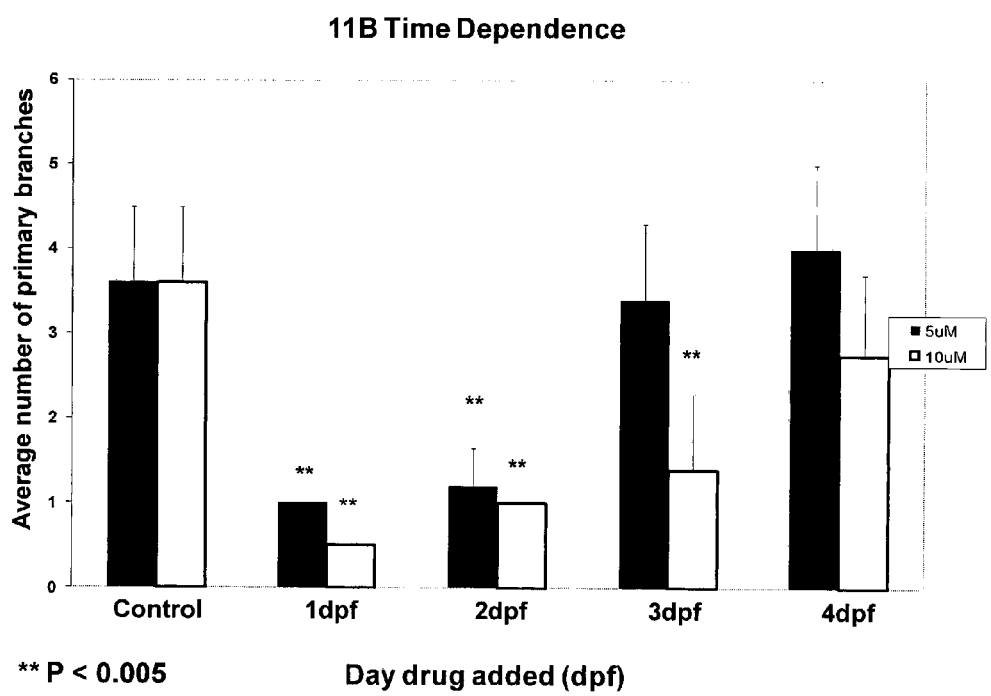
FIG. 8 shows that 11B inhibited developmental angiogenesis in the eye in a time-dependent manner. In this experiment, zebra fish were incubated with 11B at day 2, 3, 4 or 5, and all samples were prepared for analysis at day 5. At a concentration of 5 µM 11B, treatment of larvae from day 3-5 or 4-5 has no significant effect on hyaloid vasculature development. In contrast, treatment with 5 µM 11B from day 1-5 or 2-5 results in a significant reduction in the number of primary branches of hyaloid vasculature (p<0.005). Similarly, treatment with 10 µM 11B from day 4-5 dpf has no effect, whereas treatment with 10 µM 11B from day 1-5, 2-5 or 3-5 results in a significant reduction in the number of primary branches of hyaloid vasculature (p<0.005). n≥5 for all treatment groups. dpf, days post fertilisation.

The anti-angiogenic efficacy of compounds 11B and 11F has been demonstrated in the eye, in vivo. These compounds do not induce toxic effects on the larvae, the gross morphology of the larvae is normal (FIG. 7B). Further characterisation of compound 11B shows that the gross morphology of fish treated from 1-5 dpf is normal, that the morphology (layering of the retina, size of retina/lens, presence of optic nerve) of eyes in transverse sections of treated larvae is normal and that 11B has no significant effect on visual function (FIG. 9). Visual function was assessed using the optokinetic response, a behavioural assay that tests the ability of larval zebrafish to track moving stripes (Brockerhoff 2006). In addition, to a dose-dependent anti-angiogenic activity (FIG. 7), compound 11B exerted a time-dependent effect (FIG. 8). For these experiments the compounds were screened in zebrafish larvae as described above except that the drug (compound 11B) was added at either day 1, 2, 3 or 4, and all treated larvae were analysed at day 5. Finally, analyses of the intersegmental vessels of the zebrafish trunk indicated that compound 11B added from day 1-5 had no effect on the earlier formed vessels but it did effect developmental angiogenesis of hyaloid vessels (FIG. 7). This indicated that compound 11B has an effect on newly forming, but not existing vessels.

Example 5

Compounds Structurally Related to 11B and 11F Exhibit Anti-Angiogenic Activity

Figure 5:
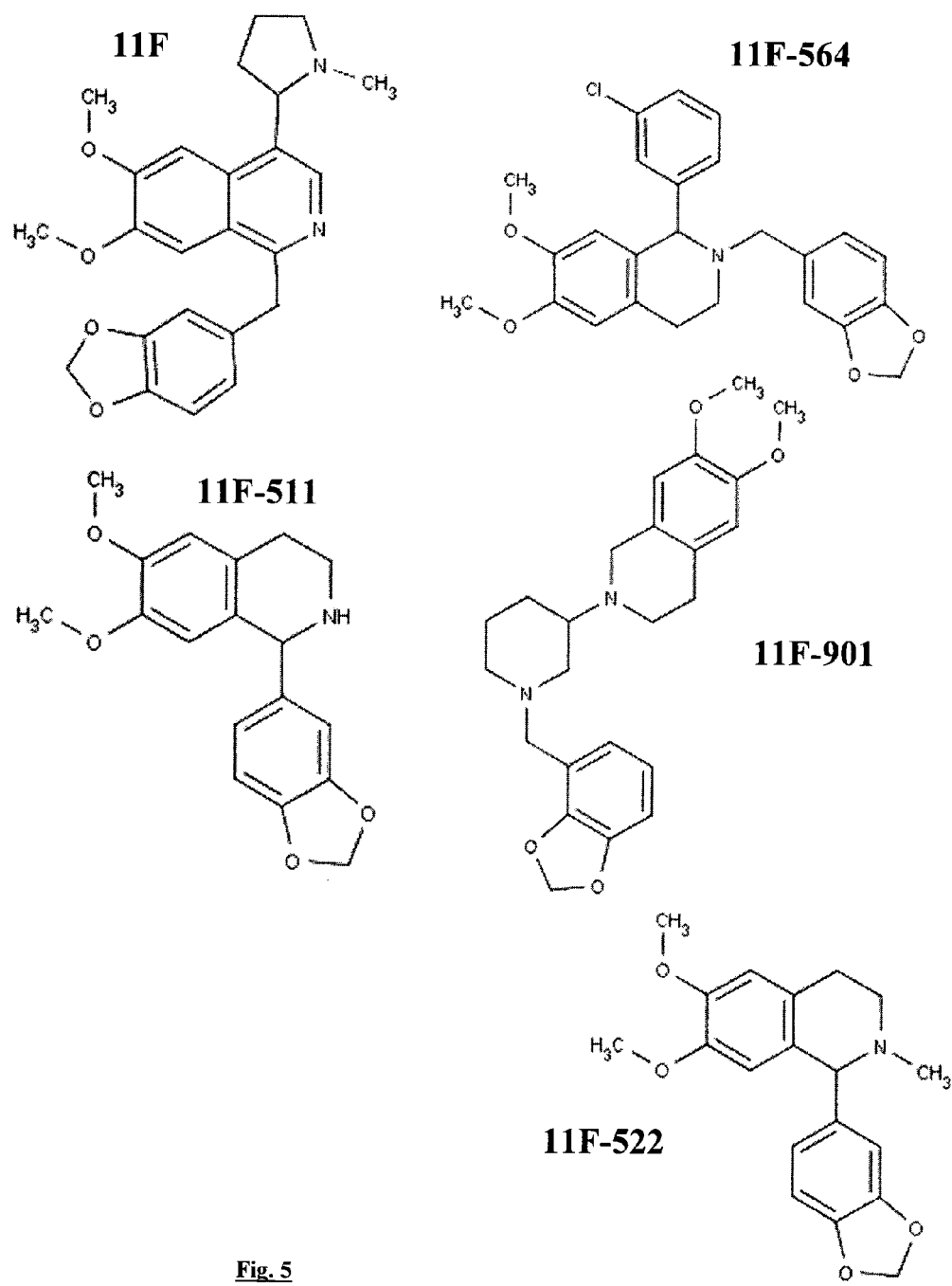
FIG. 5 shows the chemical structures of 4 compounds related to 11F that were used for a structure-activity relationship study.
Figure 6:
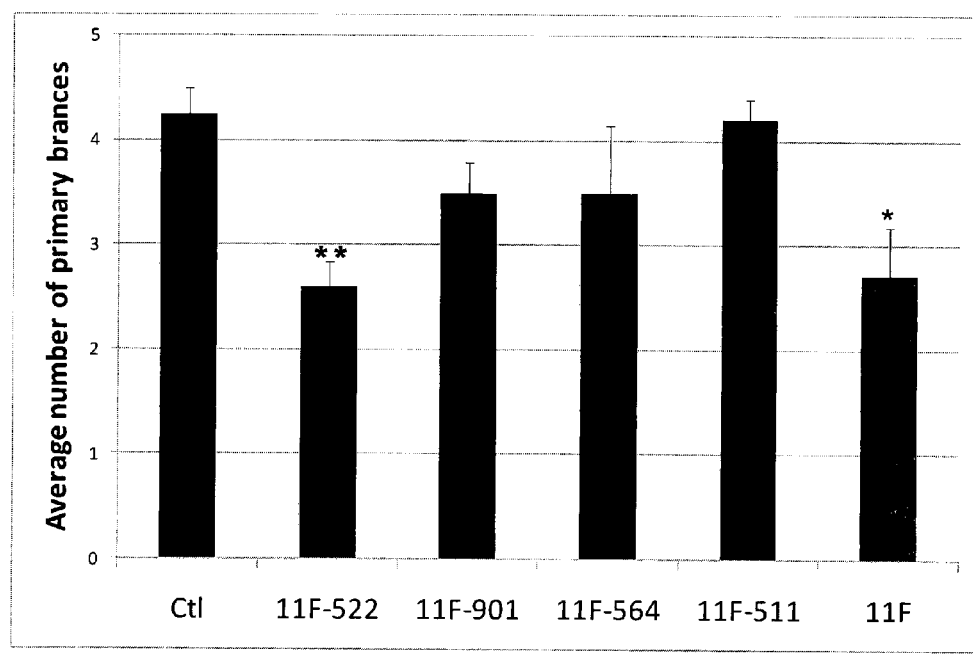
FIG. 6 shows that a compound structurally similar to 11F has a similar anti-angiogenic effect. Graph of the average number of primary branches of hyaloid vasculature following treatment of larvae with increasing concentrations of 11F or related chemical structures. 10 µM of 11F or 11F-522 results in a significant inhibition of hyaloid vasculature development (p<0.05 and p<0.005, respectively). n=4 (Ctl, 11F-901, 11F-564), n=5 (11F-522, 11F-511) and n=7 (11F), * p-value 0.0432, ** p-value 0.0023.
Figure 12:
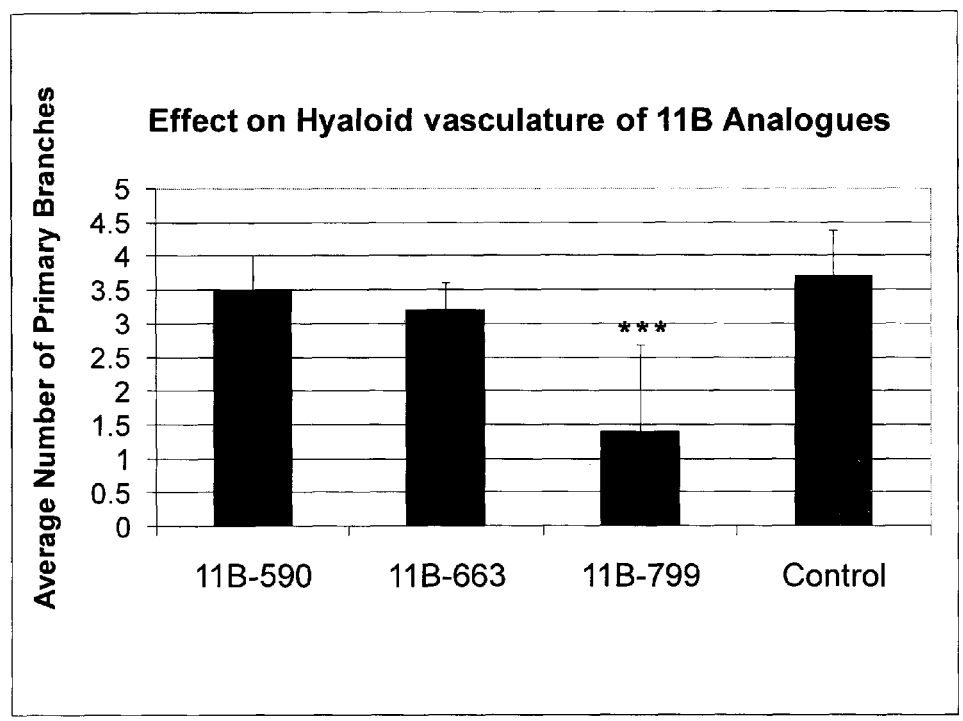
FIG. 12 shows that a compound structurally similar to 11B has a similar anti-angiogenic effect. Graph of the average number of primary branches of hyaloid vasculature following treatment of larvae with increasing concentrations of 11B or related chemical structures. Similar to 11B, 10 µM of 11B-799 results in a significant inhibition of hyaloid vasculature development (p<0.0005). n≥10 for all treatment groups.

To further validate the anti-angiogenic activity of compounds 11B and 11F, we tested several structurally related compounds in the zebrafish angiogenesis assay described above. The structures of compounds related to 11F are shown in FIG. 5 and the structures of the compounds related to 11B are shown in FIG. 11. One of the compounds related to 11F, compound 11F-522, also inhibited developmental angiogenesis of the hyaloid vasculature in vivo (FIG. 6). The chemical name of 11F-522 is 1-(1,3-benzodioxol-5-yl)-6,7-dimethoxy-2-methyl-1,2,3,4-tetrahydroisoquinoline, the structure of 11F-522 is shown below. Compound 11B-799, related to 11B, also inhibits developmental angiogenesis of the hyaloid vasculature in vivo (FIG. 12). The chemical name of 11B-799 is 4-[2-(4-quinolinyl)vinyl]phenol, the structure of 11B-799 is shown below.

Sturucture III (11F-522)

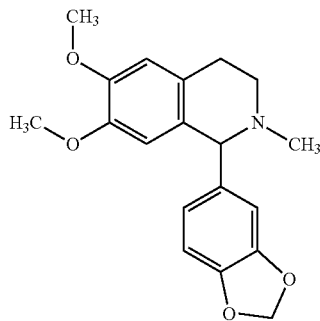

Structure IV (11B-799)

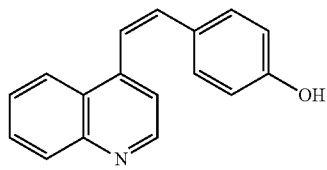

Example 6

Anti-Angiogenic Efficacy of 11F-522 Enantiomers

Figure 17:
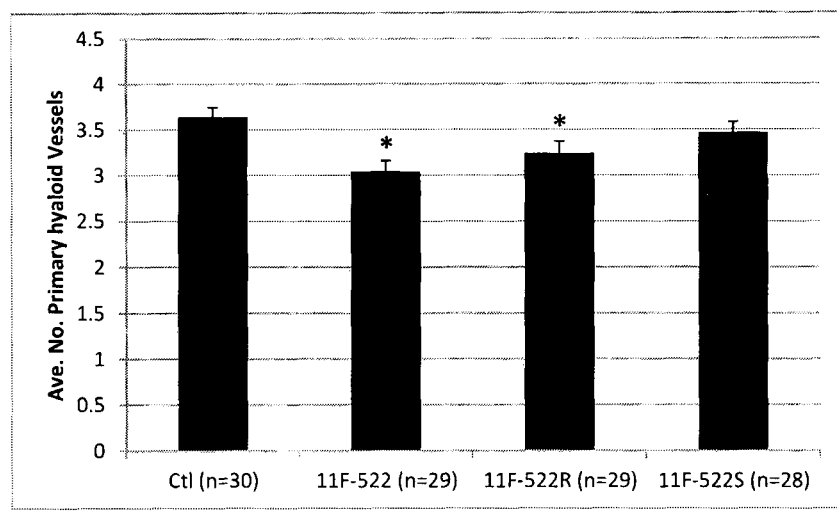
FIG. 17 shows that enantiomer 2 (11F-522R) of 11F-522 has anti-angiogenic activity. Graph of the average number of primary branches of hyaloid vasculature following treatment of larvae with 10 µM 11F-522 (racemic mixture), 10 µM 11F-522 enantiomer 1 (11F-522S) and 10 µM 11F-522 enantiomer 2 (11F-522R). 11F-522 and 11F-522 enantiomer 2 (11F-522R) significantly reduce the number of primary hyaloid vessels (p<0.05).

To determine the anti-angiogenic activity of 11F-522 enantiomers, we tested the R- and S-enantiomers in the zebrafish hyaloid angiogenesis assay described above. The structures of the 11F-522 enantiomers are shown below. The chemical name of 11F-522 is 1-(1,3-benzodioxol-5-yl)-6,7-dimethoxy-2-methyl-1,2,3,4-tetrahydroisoquinoline, the structure of 11F-522 is shown below. The structure of 11F-522 enantiomer (S)-(+)-1-(1,3-benzodioxol-5-yl)-6,7-dimethoxy-2-methyl-1,2,3,4-tetrahydroisoquinoline (Enantiomer 1 or 11F-522S) and the structure of 11F-522 enantiomer (R)-(−)-1-(1,3-benzodioxol-5-yl)-6,7-dimethoxy-2-methyl-1,2,3,4-tetrahydroisoquinoline (Enantiomer 2 or 11F-522R) are shown below. In the hyaloid angiogenesis assay 11F-522 and 11F-522R show a significant ($p<0.05$) reduction in the number of primary hyaloid vessels whereas 11F-522S did not reduce primary hyaloid vessel number ($n \geq 24$ for all samples) (FIG. 17).

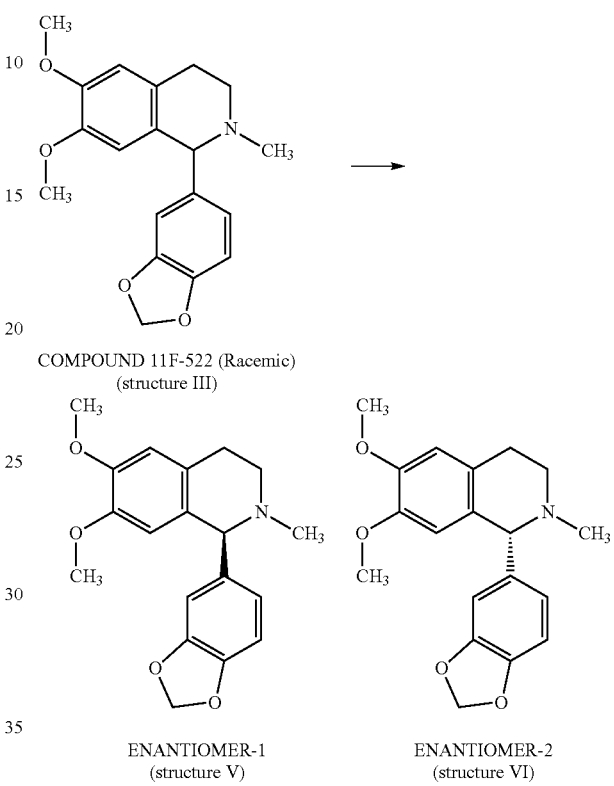

Example 7

Validation of Anti-Angiogenic Activity in Human Endothelial Cells

Figure 13:
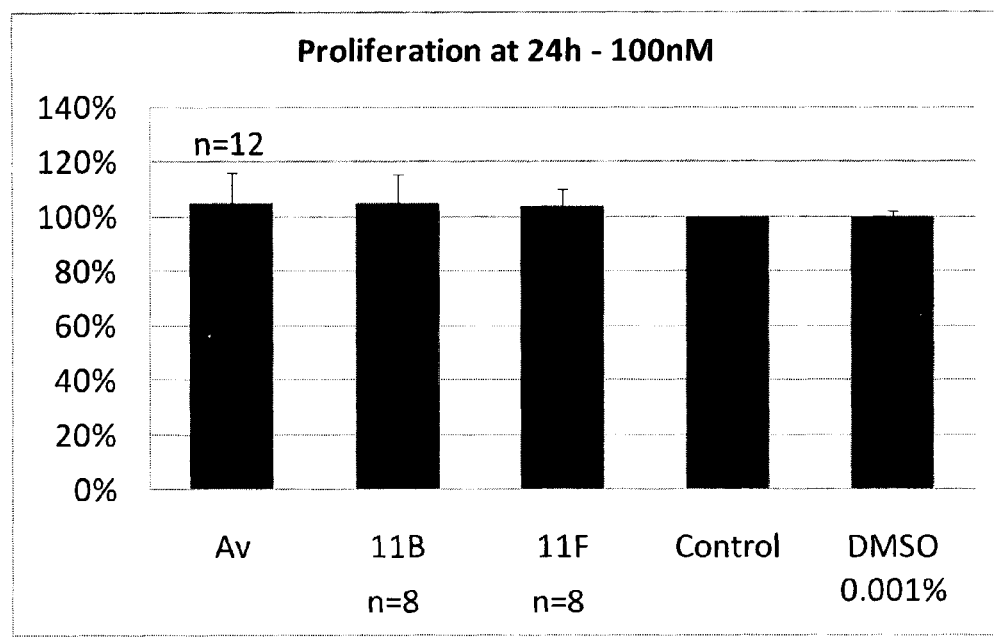
FIG. 13 shows that 11B and 11F have no significant effect on the proliferation of human endothelial cells in vitro. Cultures of dermal-derived normal human microvascular endothelial cells (HMVEC-d) were treated with 100 nM of Avastin (Bevacizumab), 11B or 11F. Similar to the clinically used anti-angiogenic Avastin (Av), neither 11B nor 11F had significant effects on endothelial cell migration compared to control or vehicle-treated (DMSO) cells. In this experiment, the effect of Avastin was compared to the control and the effect of 11B and 11F were compared to vehicle treated (DMSO cells)
Figure 14:
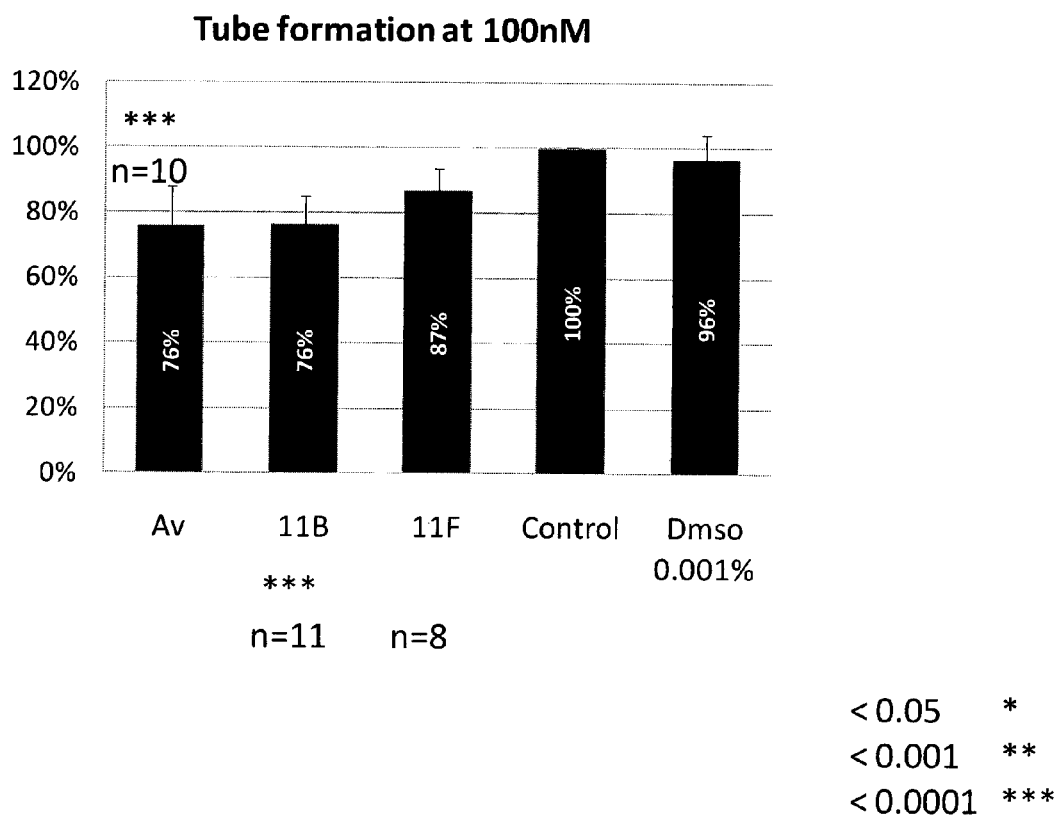
FIG. 14 shows that 11B significantly inhibits the ability of human endothelial cells to form tubules in culture (an in vitro angiogenesis assay). Cultures of dermal-derived normal human microvascular endothelial cells (HMVEC-d) were treated with 100 nM of Avastin (Bevacizumab), 11B or 11F. The clinically used anti-angiogenic Avastin (Av) and 11B significantly inhibited (~20-24% reduction) tubule formation compared to their controls, (Control and DMSO, respectively). 11F reduced tubule formation by 9% compared to its DMSO control, *** p-value<0.0001.

To demonstrate the anti-angiogenic potential of compounds 11B and 11F in human cells, we treated cultures of dermal-derived normal human microvascular endothelial cells (HMVEC-d) with 11B or 11F or with the clinically used anti-angiogenic Avastin. Compounds 11B and 11F had no significant effect on the proliferation or migration potential of HMVEC-d cultures (FIG. 13). However, compound 11B significantly inhibits the ability of HMVEC-d cells to form tubules in vitro (FIG. 14). Tubule formation is a key step in angiogenesis and this result indicates that compound 11B has anti-angiogenic activity upon human endothelial cells.

HMVEC-d were purchased from Clonetics, San Diego, Calif., USA. Cells were maintained in complete Endothelial Cell Medium (Clonetics® EGM®-2-MV BulletKit®) containing 500 ml of Endothelial Cell Basal Medium-2 and supplemented with hEGF, 0.5 ml; Hydrocortisone, 0.2 ml; GA-1000, 0.5 ml; FBS, 25 ml; VEGF, 0.5 ml; hFGF-B, 2.0 ml; R3-IGF-1, 0.5 ml; Ascorbic Acid, 0.5 ml in a 37° C. humidified atmosphere of 5% CO2/95% air. HMVEC-d were used for experiments between passages 4-8.

The responses to different compound treatments were examined using a crystal violet-based proliferation assay to test the effects of the compounds on cell proliferation.

HMVEC-d were seeded in 96-well plates in complete medium at a density of 25,000 cells/cm$^2$ and allowed to attach in a humidified atmosphere of 5% $CO_2$, 95% air and at 37° C. Cells were treated with the compounds at different concentrations in replicates wells, and cell proliferation was evaluated after 24 h. At the specific time point medium was removed, cells were fixed with 1% glutaraldehyde and stained with a 0.1% crystal violet solution (Pro-lab diagnostics) for 30 min. The plates were then washed extensively in water and air dried. Cell-associated dye was extracted with a 1% solution of Triton X100 and the absorbance was determined at 550 nm using a plate reader (Multiskan Ascent, Lab Systems). Similar to Avastin, neither 11B nor 11F had a significant effect upon HMVEC-d proliferation (FIG. 13).

Continuous monitoring of HMVEC-d cultures cell migration was recorded using a CIM-plate 16 (RTCA DP Analyser, xCELLigence System, Roche) with 5% serum serving as chemoattractant and following the manufacturer's protocol. Each well is composed of an upper chamber, a membrane with an interdigitated gold electrode on the underside of the microporous membrane (facing the lower chamber) and a lower chamber. Cells that have migrated to the lower chamber containing the chemoattractant attach to the gold electrodes and generate electrical impedance. Impedance readings are taken from an electronic sensor plate and reflect their attachment levels. Full strength EGM growth medium was added as chemoattractant in the lower chamber, and serum free media was used instead for the negative controls wells. The upper chamber was then clicked into position and 30 µl of serum-free media were added to cover the membrane surface. The CIM-plates were then placed in an incubator at 37° C. in 5% $CO_2$ humidified atmosphere for at least 1 h. In the meantime HMVEC-d cultures were removed from culture, trypsinised, and resuspended in 1% FBS EGM growth medium. A background measurement was initially taken, then 75×10$^4$ cells/well were seeded with or without treatments in replicates and the plate left under a tissue culture hood at RT for 30 min to allow the cells to settle. The CIM-plate was then loaded into a RTCA DP Analyser at 37° C. 5% $CO_2$ humidified atmosphere and the Cell Index (CI) was recorded every 15 min. On the second day the Cell index were checked and plotted using the RTCA software. Similar to Avastin, neither 11B nor 11F had a significant effect upon HMVEC-d cell migration in vitro.

In Vitro HMVEC-d Tube Formation Assays

Matrigel (Becton Dickenson) basement membrane matrix was used to examine HMVEC-d tube formation. Matrigel (50 µl) was plated in 96 well culture plate wells after thawing on ice and allowed to polymerise at 37° C. 5% $CO_2$ humidified atmosphere for 1 hr. HMVEC-d were removed from culture, trypsinised, and resuspended in full strength EGM growth medium. Cells were seeded at a density of 50×10$^4$ cells/cm$^2$ and incubated for 20 hr at 37° C. 5% $CO_2$ humidified atmosphere. Endothelial cell tubule formation was assessed using phase contrast microscopy and photographed. A connecting branch between two discrete ECs was counted as one tube. The tube analysis was determined from 3 sequential fields (magnification×10) focusing on the surface of the matrigel. Avastin (Av), the clinically used anti-angiogenic, and 11B significantly inhibited (~20-24% reduction) tubule formation compared to their controls whereas 11F reduced tubule formation by 9% compared to its control (FIG. 14).

Example 8

Figure 15:
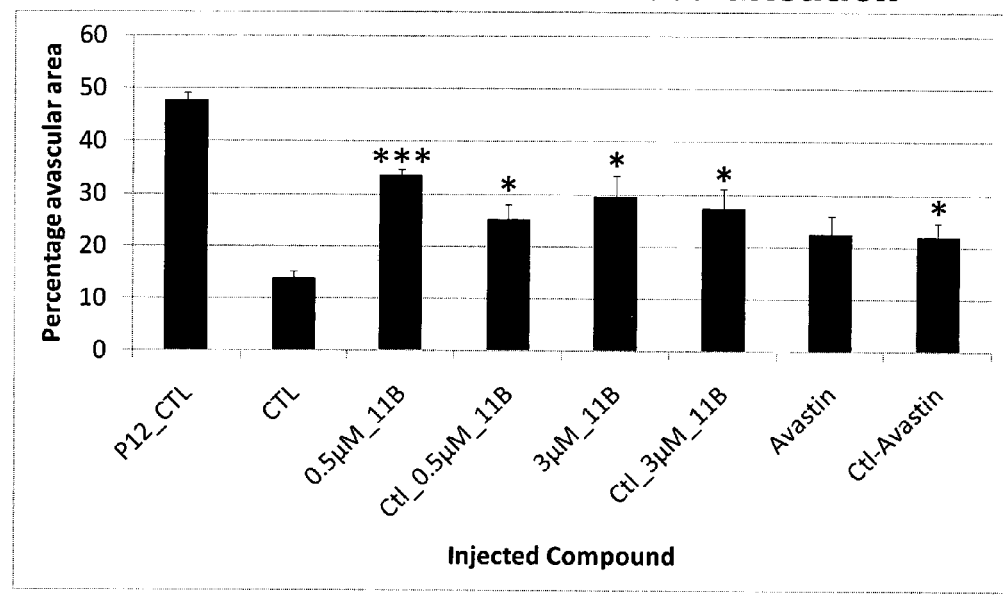
FIG. 15 shows that 11B can inhibit intraocular neovascularisation in the mouse oxygen-induced retinopathy model. Postnatal day 12 mice in hyperoxia (Ctl_P12) have an average of 47% of their retinae that is not vascularised (avascular). In contrast, transfer of equivalent mice at day 12 to normoxic conditions, which is a relatively hypoxic environment for these mice, results in significant neovascularisation of the retina by postnatal day 17 (Ctl), with only 14% of the retina avascular. Treatment of mice transferred from hyperoxia to normoxia from postnatal day 12-17 with 2 µg/µl Avastin (Bevacizumab) reduced this neovascularisation, resulting in an avascular area of ~22% of the retina in the treated eyes (Avastin) and vehicle-injected contralateral eyes (Ctl-Avastin). Significantly, treatment with 11B inhibited retinal neovascularisation, resulting in a ~33% (0.5 µM 11B) and ~30% (3 µM 11B) avascular area in treated eyes and a ~25% (Ctl_0.5 µM 11B) and ~27% (Ctl_3 µM 11B) avascular area in the vehicle-injected contralateral eyes; and n=5 (controls), n=4 (0.5 uM 11B), n=10 (3 uM 11B), n=8 (avastin).

Validation of Anti-Angiogenic Activity in a Mouse Model of Ocular Neovascularisation To assess the ability of compound 11B to inhibit ocular neovascularisation in mammalian eyes, 11B was tested in the mouse model of oxygen induced retinopathy (OIR). 11B inhibited angiogenesis in a mouse model of ocular neovascularisation (FIG. 15). 11B was injected intravitreally into a mouse model of oxygen-induced retinopathy (OIR). The OIR model was generated by placing postnatal day 7 (P7) mouse pups into hyperoxia (75% oxygen) for 5 days and then removing them to normoxia (21%) on postnatal day 12 (P12). The hyperoxic (high oxygen) environment causes retinal blood vessels to regress between P7 and P12. The normoxic environment on P12 is a relatively hypoxic (low oxygen) environment for the mice and causes the growth of new blood vessels (angiogenesis). For all samples, eyes were enucleated, fixed, flat mounted and then stained with an isolectin antibody to visualise the blood vessels. Blood vessels were quantified and those treated with lead compounds compared to controls. Relative to the avascular area in the P17 control, intraocular injections of 11B show an ~2.4 fold increase in avascular retina (i.e. inhibition of ocular neovascularisation) compared to the ~1.6 fold increase in avascular retina observed with Avastin (FIG. 15).

Example 9

11B and 11F Significantly Reduce Angiogenic/Inflammatory Factor Secretion From Human Colorectal Tumour Explants To assess the anti-cancer potential of compounds 11B and 11F, we tested their ability to modulate the levels of angiogenic/inflammatory factors secreted from explants cultures of human colorectal cancers.

Human colorectal tumour samples were taken directly from the pathology laboratory after surgery once adequate material was taken for diagnostic testing. The tumour samples were washed and stored in DMSO/tumour conditioning media (TCM). The samples were snap-frozen in liquid nitrogen and stored at −80° C. until compound testing was performed. Prior to compound testing, the tumours were thawed and incubated in fresh TCM for 24 hours. The explants were then treated with 11B, 11F and Avastin at 1 µM and 10 µm concentrations for 72 hours. The TCM solutions were collected and stored at −20° C. and the remaining tumour explants were snap-frozen in liquid nitrogen and stored at −80° C. The protein content of each tumour sample was determined using the BCA protein assay. ELISA was used to determine the levels of VEGF, IL-8, MCP-1, GRO-α, IL-1β and IL-6. The secretion data were normalised according to the tumour sample's protein content.

Avastin, a clinically used anti-angiogenic, has significant effects on the levels of vascular endothelial growth factor (VEGF) and interleukin 6 (IL-6) secreted by the human tumour explants (FIG. 16). 11B significantly reduced the levels of VEGF, IL-6 and interleukin 1 beta (IL-1β) secreted by the human tumour explants (FIG. 16). 11F significantly reduced the levels of VEGF and IL-1β, secreted by the human tumour explants (FIG. 16).

The invention is not limited to the embodiment hereinbefore described, with reference to the accompanying drawings, which may be varied in construction and detail.

REFERENCES

Alvarez Y, Astudillo O, Jensen L, Reynolds A L, Waghorne N, Brazil D P, Cao Y, O'Connor J J, Kennedy B N. 2009. Selective inhibition of retinal angiogenesis by targeting PI3 kinase. PLoS One 4:e7867.

Alvarez Y, Cederlund M L, Cottell D C, Bill B R, Ekker S C, Torres-Vazquez J, Weinstein B M, Hyde D R, Vihtelic T S, Kennedy B N. 2007. Genetic determinants of hyaloid and retinal vasculature in zebrafish. BMC Dev Biol 7:114.

Bergers G, Benjamin L E. 2003. Tumorigenesis and the angiogenic switch. Nat Rev Cancer 3:401-410.

Bergers G, Hanahan D. 2008. Modes of resistance to anti-angiogenic therapy. Nat Rev Cancer 8:592-603.

Brockerhoff S E. 2006. Measuring the optokinetic response of zebrafish larvae. Nat Protoc 1:2448-2451.

Carmeliet P. 2005. VEGF as a key mediator of angiogenesis in cancer. Oncology 69 Suppl 3:4-10.

Culy C. 2005. Bevacizumab: antiangiogenic cancer therapy. Drugs Today (Bare) 41:23-36.

den Hertog J. 2005. Chemical genetics: Drug screens in Zebrafish. Biosci Rep 25:289-297.

Doukas J, Mahesh S, Umeda N, Kachi S, Akiyama H, Yokoi K, Cao J, Chen Z, Dellamary L, Tam B, Racanelli-Layton A, Hood J, Martin M, Noronha G, Soll R, Campochiaro P A. 2008. Topical administration of a multi-targeted kinase inhibitor suppresses choroidal neovascularization and retinal edema. J Cell Physiol 216:29-37.

Ellis L M. 2003. Antiangiogenic therapy at a crossroads: clinical trial results and future directions. J Clin Oncol 21:281s-283s.

Ferrara N. Vascular endothelial growth factor and age-related macular degeneration: from basic science to therapy. Nat Med 16:1107-1111.

Ferrara N, Kerbel R S. 2005. Angiogenesis as a therapeutic target. Nature 438:967-974

Frank R N. 2004. Diabetic retinopathy. N Engl J Med 350:48-58.

Goldsmith P. 2004. Zebrafish as a pharmacological tool: the how, why and when. Curr Opin Pharmacol 4:504-512.

He A R, Marshall J. 2005. Biologic therapy for colon cancer. Clin Adv Hematol Oncol 3:555-561.

Jager R D, Mieler W F, Miller J W. 2008. Age-related macular degeneration. N Engl J Med 358:2606-2617.

Kleinman M E, Yamada K, Takeda A, Chandrasekaran V, Nozaki M, Baffi J Z, Albuquerque R J, Yamasaki S, Itaya M, Pan Y, Appukuttan B, Gibbs D, Yang Z, Kariko K, Ambati B K, Wilgus T A, DiPietro L A, Sakurai E, Zhang K, Smith J R, Taylor E W, Ambati J. 2008. Sequence- and target-independent angiogenesis suppression by siRNA via TLR3. Nature 452:591-597.

MacRae C A, Peterson R T. 2003. Zebrafish-based small molecule discovery. Chem Biol 10:901-908.

Mandala M, Ferretti G, Barni S. 2004. Oxaliplatin in colon cancer. N Engl J Med 351:1691-1692; author reply 1691-1692.

Nagarajan K, Chandrasekharan J, and Rodrigues P J, 1994. Some observations on the enantio- and diastereo-selective synthesis of 1-substituted-1,2,3,4-tetrahydro isoquinolines. Journal of the Indian Institute of Science 74 (2): 247-256

Narayanan R, Kuppermann B D, Jones C, Kirkpatrick P. 2006. Ranibizumab. Nat Rev Drug Discov 5:815-816.

Peterson R T, Shaw S Y, Peterson T A, Milan D J, Zhong T P, Schreiber S L, MacRae C A, Fishman M C. 2004. Chemical suppression of a genetic mutation in a zebrafish model of aortic coarctation. Nat Biotechnol 22:595-599.

Pichler F B, Laurenson S, Williams L C, Dodd A, Copp B R, Love D R. 2003. Chemical discovery and global gene expression analysis in zebrafish. Nat Biotechnol 21:879-883.

Rattner A, Nathans J. 2006. Macular degeneration: recent advances and therapeutic opportunities. Nat Rev Neurosci 7:860-872.

Takahashi K, Saishin Y, Saishin Y, King A G, Levin R, Campochiaro P A. 2009. Suppression and regression of choroidal neovascularization by the multitargeted kinase inhibitor pazopanib. Arch Ophthalmol 127:494-499.

Wong S F. 2005. Cetuximab: an epidermal growth factor receptor monoclonal antibody for the treatment of colorectal cancer. Clin Ther 27:684-694.

Zon L I, Peterson R T. 2005. In vivo drug discovery in the zebrafish. Nat Rev Drug Discov 4:35-44.

The invention claimed is:

1. A method for the treatment of an angiogenesis-related disease or disorder comprising the step of administering a compound of structure I or IV or a salt thereof wherein the angiogenic related disease or disorder is associated with neovascularization of the eye

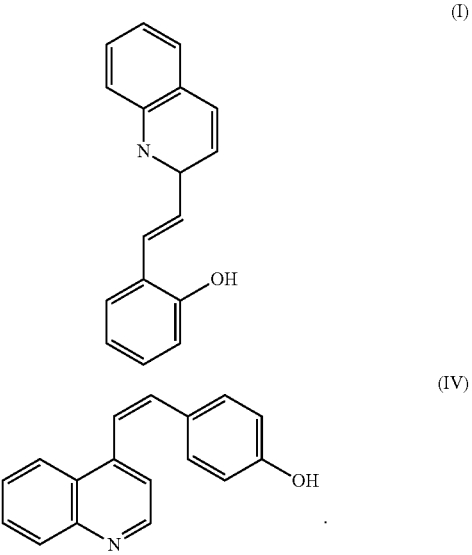

2. The method as claimed in claim 1 wherein the angiogenesis-related disease or disorder is associated with blindness.

3. The method as claimed in claim 1 wherein the angiogenesis-related disease or disorder is age-related macular degeneration or diabetic retinopathy.

4. The method as claimed in claim 1 wherein the age-related macular degeneration is wet age-related macular degeneration.

5. A pharmaceutical composition comprising a compound of structure I or IV or a salt thereof

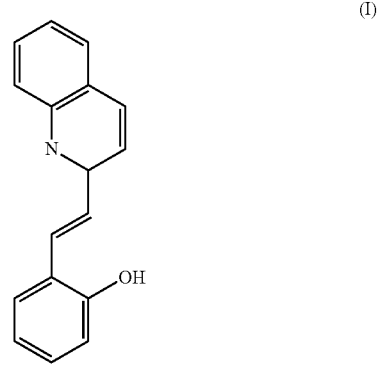

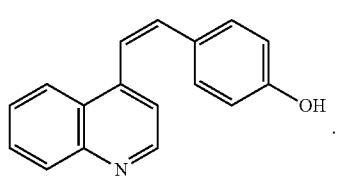
(IV)

6. The composition as claimed in claim 5 further comprising a pharmaceutically acceptable excipient.

7. The composition as claimed in claim 5 in a form for topical administration.

8. The composition as claimed in claim 5 in the form of eye drops.

9. The composition as claimed in claim 5 in a form for systemic administration.

10. The composition as claimed in claim 5 in the form of an injectable solution or suspension.

* * * * *